US006863896B1

(12) United States Patent  
O'Hagan et al.

(10) Patent No.: US 6,863,896 B1
(45) Date of Patent: Mar. 8, 2005

(54) PLANT LECTINS AS MUCOSAL ADJUVANTS

(75) Inventors: Derek O'Hagan, Berkeley, CA (US); Edward C. Lavelle, Dublin (IE)

(73) Assignee: Chiron Corporation, Emeryville, CA (US)

( * ) Notice: Subject to any disclaimer, the term of this patent is extended or adjusted under 35 U.S.C. 154(b) by 389 days.

(21) Appl. No.: 09/696,194

(22) Filed: Oct. 26, 2000

Related U.S. Application Data

(60) Provisional application No. 60/161,371, filed on Oct. 26, 1999.

(51) Int. Cl.[7] .............................................. A61K 45/00
(52) U.S. Cl. .................. 424/278.1; 530/370; 424/231.1
(58) Field of Search .......................... 424/278.1, 231.1; 530/370

(56) References Cited

U.S. PATENT DOCUMENTS

| | | | | |
|---|---|---|---|---|
| 4,414,201 A | * | 11/1983 | Shionoya et al. | ............. 424/88 |
| 4,470,967 A | * | 9/1984 | Gough et al. | .................. 424/89 |
| 5,445,818 A | * | 8/1995 | Hodges et al. | ............ 424/184.1 |
| 5,603,960 A | * | 2/1997 | O'Hagan et al. | ............ 424/501 |
| 5,629,011 A | | 5/1997 | Illum | |
| 5,744,155 A | * | 4/1998 | Friedman et al. | ............ 424/434 |
| 5,800,832 A | | 9/1998 | Tapolsky et al. | |
| 5,804,212 A | | 9/1998 | Illum | |
| 5,814,329 A | | 9/1998 | Shah | |
| 5,876,761 A | | 3/1999 | Bodmer et al. | |
| 5,955,097 A | | 9/1999 | Tapolsky et al. | |
| 5,962,428 A | * | 10/1999 | Carrano et al. | ................ 514/44 |

FOREIGN PATENT DOCUMENTS

| | | |
|---|---|---|
| DE | 42 21 836 A1 | 1/1994 |
| EP | 156 633 | 10/1985 |
| WO | 86/06635 | 11/1986 |
| WO | 92/17167 | 10/1992 |

OTHER PUBLICATIONS

Lavelle et al., "Mistletoe lectins enhance immune responses to intranasally co–administered herpes simplex virus glycoprotein D2," *Immunology 107*, 268–74, 2002.
E.C.Lavelle, et al., "Mucosal Immunogenicity of Plant Lectins in Mice", Immunology, 2000, vol. 99, pp. 30–37.
Paul J. Giannasca, et al., "Targeted Delivery of Antigen to Hamster Nasal Lymphoid Tissue with M–cell–Directed Lectins", Infection and Immunity, Oct. 1997, pp. 4288–4298.
Neil A. Williams, et al., "Immune Modulation by the Cholera–Like Enterotoxins: From Adjuvant to Therapeutic", Immunology Today, Feb. 1999, vol. 20, No. 2, pp. 95–101.
Wim Van den Broeck, et al., "Receptor–Dependent Immune Responses in Pigs after Oral Immunization with F4 Fimbriae", Infection and Immunity, Feb. 1999, pp. 520–526.
H. J. de Aizpurua, et al., "Oral Vaccination: Identification of Classes of Proteins that Provoke an Immune Response upon Oral Feeding", J. Exp. Med., Feb. 1998, vol. 167, pp. 440–451.
Naoto Shibuya, et al., "The Elderberry (*Sambucus nigra* L.) Bark Lectin Recognizes the Neu5Ac(α2–6)Gal/GalNAc Sequence", The Journal of Biological Chemistry, Feb. 5, 1987, vol. 262, No. 4, pp. 1596–1601.
Tomás Girbés, et al., "Isolation and Partial Characterization of Nigrin B, a Non–toxic Novel Type 2 Ribosome–Inactivating Protein from the Bark of *Sambucus nigra* L.", Plant Molecular Biology, 1993, vol. 22, pp. 1181–1186.
Lavelle et al., "Mucosal Immunologenicity and Adjuvanticity of Plant Lectins"*Scandinavian Journal of Immunology 52*(4) :422, Oct., 2000.
O'Hagan et al., "Intranasal Immunization with Recombinant gD2 Reduces Disease Severity and Mortality Following Genital Challenge with Herpes Simplex Virus Type 2 in Guinea Pigs" *Vaccine 17*:2229–2236, 1999.
Stein et al., "Induction of Anti–Mistletoe Lectin Antibodies in Relation to Different Mistletoe Extracts" *Anti–Cancer Drugs 8* (Suppl 1):S57–S59.
Lavelle et al., "The Identification of Plant Lectins with Mucosal Adjuvant Activity" *Immunology 102*:77–86, 2001.

* cited by examiner

Primary Examiner—Jeffrey S. Parkin
(74) Attorney, Agent, or Firm—Lisa M. Hemmendinger; Rebecca M. Hale; Robert P. Blackburn

(57) ABSTRACT

The invention provides a method of increasing an immune response in a mammal. The method involves administering to the mammal an admixture comprising an immunogen and a plant lectin. The plant lectin acts as an adjuvant to increase an immune response against the immunogen. The method is especially well-suited for mucosal administration to humans and other mammals.

37 Claims, 29 Drawing Sheets

PLANT LECTINS AS MUCOSAL ADJUVANTS

This application claims the benefit of provisional application Ser. No. 60/161,371 filed Oct. 26, 1999, which is incorporated herein by reference.

TECHNICAL FIELD OF THE INVENTION

The invention relates to the enhancement of an immune response in a mammal. More particularly, the invention relates to the use of plant lectins as adjuvants.

BACKGROUND OF THE INVENTION

Because most pathogens colonize and invade the host at mucosal surfaces, the induction of immunity at these sites is a rational and attractive approach to prevent infection (1). Mucosal routes for vaccine delivery are non-invasive, so administration is relatively simple and inexpensive. Furthermore, the potential to induce a range of mucosal and systemic immune responses after mucosal vaccine delivery allows the possibility of effective immunization against many diseases. For example, specific IgA alone can protect mice against intranasal infection with influenza (2) and intestinal infection with Vibrio cholerae (3). However, mucosal delivery of nonreplicating immunogens typically does not stimulate strong immune responses. Where responses are induced, the delivery of multiple high doses is often necessary (4). In addition, mucosal delivery of immunogens frequently results in systemic unresponsiveness (1).

A number of strategies may be used to enhance responses to mucosally delivered vaccines. Live bacterial and viral vectors which colonize the mucosae can be used to deliver immunogens (5). Imparting particulate characteristics to immunogens by association with biodegradable microparticles (6) or liposomes (7) can also enhance mucosal immunogenicity.

Another approach is the use of lectin-like molecules with adjuvant properties. The most powerful mucosal adjuvants identified to date are cholera toxin produced by Vibrio cholerae (CT) and heat-labile enterotoxin (LT) from enterotoxigenic strains of Escherichia coli (8, 9). CT and LT are well-characterized mucosal immunogens and adjuvants for bystander proteins. These toxins contain separate A and B subunits (referred to as CTA and CTB, respectively). The B subunits mediate binding to cell surface receptors (20). GM1 ganglioside is considered to be the principal receptor for CT (21), but CTB may bind to cell surface receptors other than GM1 (22). After binding of the B subunit, the A subunit reaches the cytosol and activates adenyl cyclase leading to a large increase in $[cAMP]_i$ (10, 11). LT is structurally and functionally similar to CT and is comparable to CT as a systemic or mucosal adjuvant (23, 24). In mice, CT strongly stimulates humoral and cell-mediated immune responses, including mucosal IgA production and cytotoxic T cell effector functions (10). Stimulation of toxin-specific local and systemic responses and responses to co-administered immunogens distinguish these molecules from most soluble proteins which are poorly immunogenic when administered mucosally (10, 11). The toxicity of these molecules, however, prevents clinical application.

Certain plant lectins have been investigated as agents for specific targeting of molecules to a mucosal epithelium. Plant lectins are proteins containing at least one non-catalytic domain, which binds specifically and reversibly to a monosaccharide or oligosaccharide (13). For example, Giannasca et al. (14) discloses that intranasal immunization with a lectin-immunogen conjugate stimulated induction of specific IgG antibodies, while immunogen alone or admixed with lectin did not. U.S. Pat. No. 4,470,967 discloses that a complex of a glycoprotein immunogen with a lectin can act as an adjuvant to increase the immune response against the immunogen. Similarly, WO 86/06635 discloses a chemically modified immunogen-lectin complex which can be used to elicit an immune response in vertebrates, including mammals. In each of these cases, however, the lectin was physically coupled to the immunogen. This requires at least one extra preparation step and may actually alter an epitope of the immunogen against which an immune response is desired, such as an epitope against which a neutralizing immune could be directed.

Thus, there is a need in the art for simple, effective, and non-toxic methods of increasing immune responses in a mammal, particularly after mucosal administration, without the need to complex the immunogen with another molecule and potentially mask or alter desirable epitopes.

SUMMARY OF THE INVENTION

The invention provides a method of increasing an immune response in a mammal by administering to the mammal an admixture comprising an immunogen and a plant lectin. The mammal thereby produces an immune response which is increased relative to an immune response produced in the absence of the plant lectin.

The invention thus provides a simple and effective method of increasing an immune response in a mammal.

BRIEF DESCRIPTION OF THE DRAWINGS

FIG. 2A, serum IgG titers after one dose (day 13). FIG. 2B, serum IgG titers after two doses (day 27). FIG. 2C, serum IgG titers after three doses (day 41). FIG. 2D, serum IgG titers after the final dose (day 56).

FIG. 4A, saliva; FIG. 4B, vaginal wash; FIG. 4C, nasotracheal wash; FIG. 4D, intestinal wash.

FIG. 5A, CT; FIG. 5B, LEA; FIG. 5D, PHA; FIG. 5E, WGA; FIG. 5F, UEA-I.

FIG. 6A, day 14; FIG. 6B, day 28; FIG. 6C, day 41; FIG. 6D, day 55.

FIG. 7A, IgG1; FIG. 7B, IgG2a; FIG. 7C, IgG2b; FIG. 7D, IgG3.

FIG. 8A, saliva; FIG. 8B, vaginal wash; FIG. 8C, nasotracheal wash; FIG. 8D, intestinal wash.

FIG. 9. gD2-specific total serum IgG and IgG subclass titers from mice immunized intransally on days 1, 21, and 42 with either gD5 (5 μg) alone or gD2 (5 μg) together with 1 μg of CT, ML-I, Nigrin B, Basic Nigrin B, Ebulin r1, SNA II or SELfd. FIG. 9C, IgG2a.

FIG. 10. gD2-specific IgA antibody titers measured in secretions of mice immunized intranasally on days 1, 21, and 42 with either gD2 (5 μg) alone or gD2 (5 μg) together with 1 μg of CT, ML-I, Nigrin B, Basic Nigrin B, Ebulin r1, SNA II or SELfd.

FIG. 11. gD2-specific serum IgA and IgG antibody titers measured in mice immunized intranasally on days 1, 21, and 42 with either gD2 (5 μg) alone or gD2 (5 μg) together with 1 μg of CT, ML-I, or UEA-1.

FIG. 12. gD2-specific IgG subclass antibody titers measured in mice immunized intranasally on days 1, 21, and 42 with either gD2 (5 μg) alone or gD2 (5 μg) together with 1 μg of CT, ML-I, or UEA-1. FIG. 12B, IgG2a.

FIG. 13. gD2-specific IgA antibody titers measured in secretions of mice immunized intranasally on days 1, 21 and 42 with either gD2 (5 μg) alone or gD2 (5 μg) together with 1 μg of CT, ML-I, or UEA-1.

FIG. 14. Mean concentrations of IL-5, IL-4, and IFN production and counts per minute for T cell proliferation assay.

FIG. 15. OVA-specific serum IgG antibody titers from mice immunized by gavage on days 1, 14, 28 and 49 with either OVA (5 mg) alone or OVA (5 mg) together with CT (10 μg), ML-I (10 μg), ML-II (10 μg) or ML-III (10 μg).

FIG. 16. OVA-specific serum IgG subclass and IgA antibody titers measured in mice immunized by gavage on days 1, 14, 35, and 49 with either OVA (5 mg) alone or OVA (5 mg) together with CT (10 μg), ML-I (10 μg), ML-II (10 μg), or ML-III (10 μg). FIG. 16B, IgG2a.

DETAILED DESCRIPTION

Figure 1:
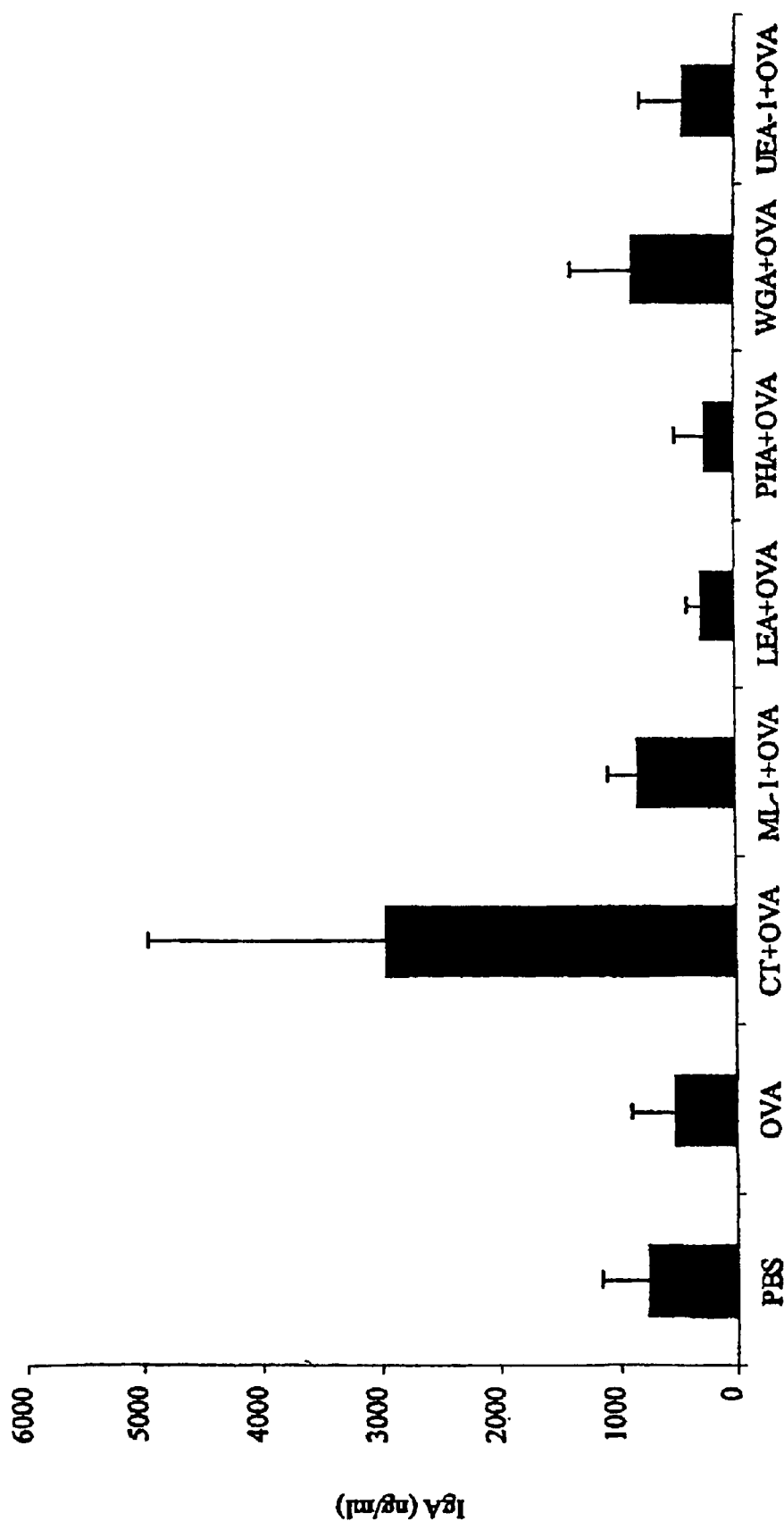
FIG. 1. Bar graph showing total IgA levels (ng/ml) measured in nasotracheal washes of mice after four intranasal doses of immunogen.
Figure 2A:
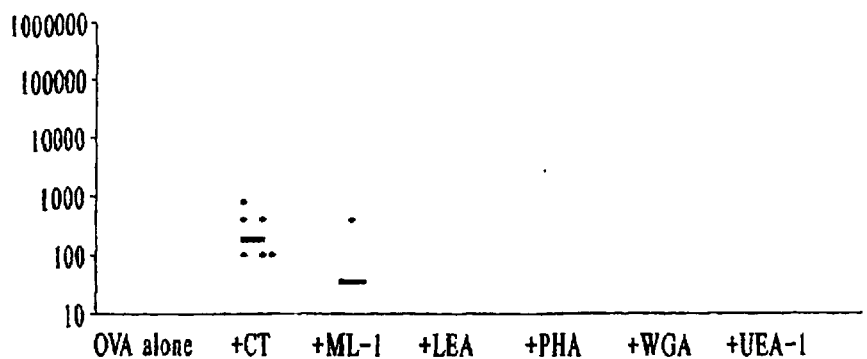
FIGS. 2A–D. Plots showing the adjuvant effect of plant lectins. OVA-specific serum IgG antibody titers from mice immunized intranasally.
Figure 2B:
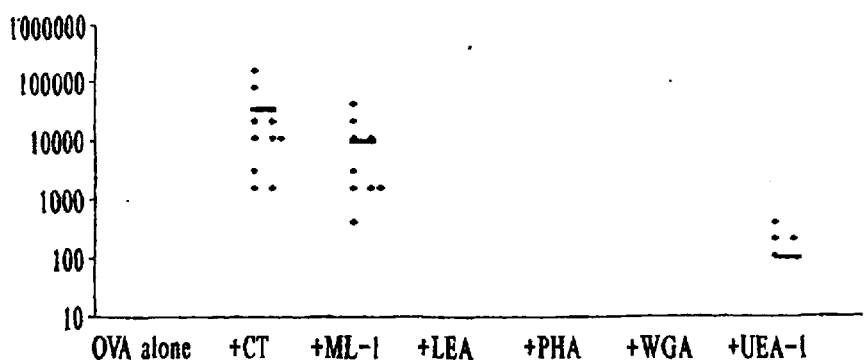
Figure 2C:
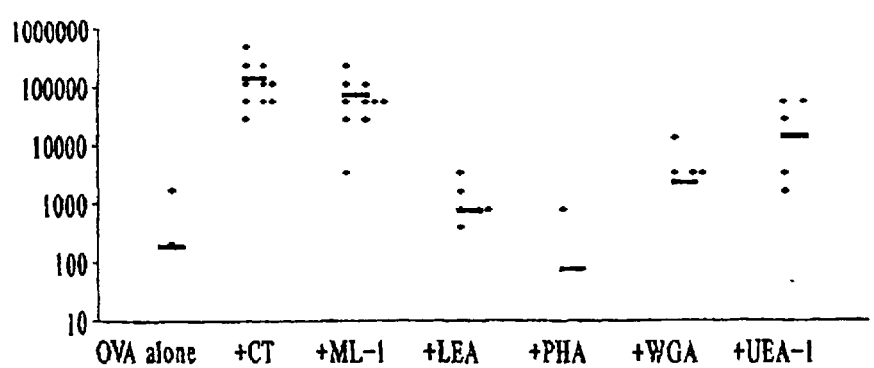
Figure 2D:
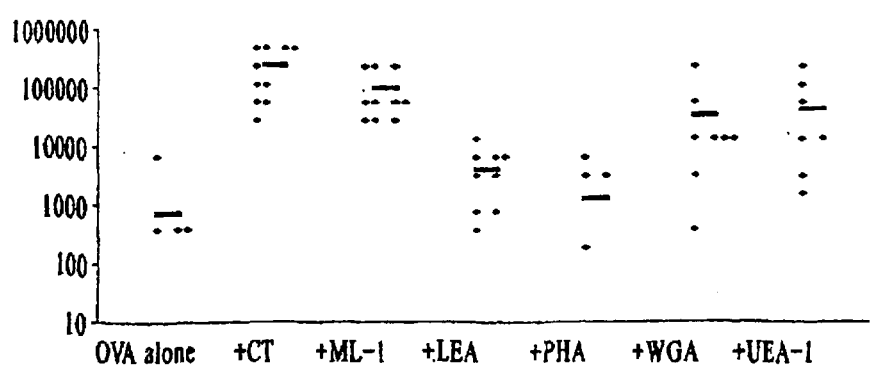

It is an aspect of the present invention that certain plant lectins act as mucosal adjuvants to increase immune responses, including an increased antibody titer, against a variety of immunogens, thus permitting simple, non-toxic, and cost-effective vaccine or immunogenic compositions to be prepared. Vaccine or immunogenic compositions of the invention are admixtures comprising a plant lectin and an immunogen. Such admixtures are especially suitable for mucosal delivery to mammals, including humans, and are thus useful for veterinary as well as human medical purposes.

Admixtures of the invention comprise a plant lectin and an immunogen. The immunogen and the lectin are not coupled together chemically, but are simply mixed together in an appropriate liquid medium, such as phosphate buffered saline or other isotonic saline solution. Optionally, an admixture can comprise stabilizing agents, including anti-microbial agents, preservatives, and the like. The proportions of immunogen and lectin in the admixture can be varied, such as at least about 1:1, 2:1, 3:1, 4:1, 5:1, 6:1, 7:1, 8:1, 9:1, or 10:1, depending on the particular immunogen and lectin combination selected. If desired, at least 2, 3, 4, or more different immunogens and/or lectins in varying proportions can be included in an admixture.

Lectins useful in the invention include plant lectins such as mistletoe lectin I (ML-I), mistletoe lectin II (ML-II), mistletoe lectin III (ML-III), wheat germ agglutinin (WGA), and Ulex europaeus (UEA-1). Other lectins which may be useful include lentil bean lectin, jack bean lectin (concanavalin A), and asparagus pea, broad bean, camel's foot tree, castor bean, fava bean, hairy vetch, horse gram, Japanese wisteria, Jequirity, Scotch laburnum, lima beam, lotus, mung bean, Osage orange, Pagoda tree, garden pea, potato, red kidney bean, Siberian pea tree, spindle tree, sweet pea, tomato, and winged pea lectins.

Type 2 ribosome inactivating proteins (RIP), such as nigrin b, basic nigrin b, ebulin l, ebulin r, ebulin f, nigrin f, SNA1, SNA1, SNAV, SNAVI, Sambucus nigra SNLRP1, SNLRP2, ricin, Ricinus lectin, Polygonatum RIP, Sieboldin-6, abrin, abrin 11, modeccin, volkensin, SSA, Cinnamonin, porrectin, gelorin, *Evanthis hyemalis*, RIP, Iris agglutinin, ML-I, ML-II, and ML-III, are especially useful as adjuvants. Such lectins contain an N-glycosidase A subunit responsible for the ribosome-inactivating activity and a galactose-specific carbohydrate-binding B subunit (29). ML-I, ML-II, and ML-III are strong mucosal adjuvants, which can stimulate high antibody titers in sera and mucosal secretions. Type 2 RIPs which do not show in vivo toxicity, such as ebulin-1 (32), nigrin b (33) and basic nigrin b (34), are particularly useful. Alternatively, lectins can be genetically "detoxified," for example by modifying one or more amino acids by site-directed mutagenesis such that the lectins retain their adjuvant properties but are non-toxic to the mammalian recipient (see 35–39; EP 0880361; EP 620850; EP 95/903889.4).

Lectins in an admixture are preferably in an unbound, water-soluble form. Suitable lectins for use in admixtures of the invention can be purchased from commercial suppliers, such as Sigma. Alternatively, lectins can be purified using protein purification protocols well known in the art, including size exclusion chromatography, ammonium sulfate fractionation, ion exchange chromatography, affinity chromatography, crystallization, electrofocusing, and preparative gel electrophoresis.

Immunogens against which a cellular and/or humoral response can be increased using a plant lectin adjuvant include proteins of infectious agents, such as viruses, bacteria, mycoplasmas, prions, and yeast, as well as hormones, allergens such as grass, weed, tree, and plant pollens, epithelia of animals such as cats, dogs, rats, and pigs, house dust, and wheat chaff. Means of obtaining such immunogens are well known in the art. An immunogen need not be able to raise a cellular and/or humoral response in the absence of the plant lectin.

Admixtures of the invention can be administered to a recipient mammal in a variety of formulations. For example, admixtures can be entrapped in or adsorbed to the surface of microparticles, such as poly(lactide-co-glycolides) (PLG) (35; U.S. Pat. Nos. 5,804,212, 6,876,761, and 5,603,960; PCT/US99/17308). Admixtures can also be administered in conjunction with bioadhesive polymers, such as those described in PCT/US99/12105, PCT/US99/11906, and U.S. Pat. Nos. 5,955,097, 5,800,832, 5,744,155, and 5,814,329. Alternatively, enteric formulations of admixtures can be used for oral administration (see U.S. Pat. No. 5,968,554).

An admixture of the invention can be administered to a mammal by injection, i.e., subcutaneous, intramuscular, or other parenteral injection, such as transdermal or transcutaneous injection, by oral ingestion, or by intranasal administration. Admixtures can be administered to any mammal in which it is desired to increase an immune response, including but not limited to rats, cats, dogs, rabbits, horses, cows, mice, guinea pigs, chimpanzees, baboons, and humans.

Mucosal administration, particularly intranasal administration into either one or both nostrils, is preferred. Doses can be delivered, for example, in one or more drops or using a spray, such as an aerosol or non-aerosol spray. If desired, multiple administrations of an admixture can be used to increase antibody titers against a particular immunogen. Intervals between multiple administrations can be at least 1, 2, 3, 4, 5, 6, or 7 or more days, or at least 2, 3, or 4 or more weeks, depending on the particular immunogen and/or lectin in the admixture. The volume of admixture to be administered will vary according to the mode of administration and size of the mammal. Typical volumes for intranasal administration vary from at least 5, 10, 15, 25, 50, 75, 100, 200, or 250 $\mu$l, to at least 500 $\mu$l or more per intranasal dose.

The concentration of immunogen in an admixture also will vary according to the particular immunogen and route of administration selected. For intranasal administration, for example, the concentration of an immunogen in an admixture varies from at least 0.033, 0.67, 0.1, 0.2, 0.33, 0.5, 0.67, 0.75, 1, 2, 2.5, 5, 7.1, 10, 12.5, 15, 17.5, 20, or 25 $\mu$g/$\mu$l.

Admixtures of the invention preferably increase antibody production as well as T cell responses, including cytokine production, target-cell killing, macrophage activation, B-cell activation, and lymphokine production. Admixtures of the invention preferably increase a T cell response or an antibody titer by at least 10, 15, 20, 25, 30, 40, 50, 75, or 100 percent or more relative to such responses to the immunogen alone in the absence of the plant lectin.

Methods of measuring T cell responses are well known in the art. (See Janeway et al., eds., 1997, IMMUNOBIOLOGY: THE IMMUNE SYSTEM IN HEALTH AND DISEASE, 3d ed., at pages 2:31–2–33; Abbas et al., 1997, CELLULAR AND MOLECULAR IMMUNOLOGY, 3d ed., at pages 250–277 and 290–293).

According to the invention, antibodies can be produced which are directed against the immunogen in the admixture. Antibodies which specifically bind to the immunogen typically provide a detection signal at least 5-, 10-, or 20-fold higher than a detection signal provided with other proteins when used in immunochemical assays, such as Western blots, ELISAs, radioimmunoassays, immunohistochemical assays, immunoprecipitations, or other immunochemical assays known in the art. Preferably, antibodies which specifically bind to a particular immunogen do not detect other proteins in immunochemical assays and can precipitate the immunogen from solution.

Antibody titer is preferably measured by ELISA, as described in Example 1, below. IgG, including IgG subtypes IgG1, IgG2a, IgG2b, and IgG3, as well as IgA antibodies directed against the immunogen can be measured in serum, in saliva, and in mucosal secretions, including vaginal, nasal, and gut washes (see Example 1).

The complete contents of all patents and patent applications cited in this disclosure are expressly incorporated herein.

The following examples are provided for exemplification purposes only and are not intended to limit the scope of the invention which has been described in broad terms above.

EXAMPLE 1

Materials and Methods

Immunogens and lectins. Cholera toxin (CT), ovalbumin (OVA, type V, hen egg) and WGA were obtained from Sigma (Poole, UK). PHA from kidney bean was prepared as described previously (15). UEA-I and LEA were obtained from Vector Laboratories. ML-I was isolated as described previously (16).

Animals. Eight week old female Balb/c mice (Harlan Olac, Bicester, UK) were given free access to commercial stock diet (Labsure, Manea, UK) and water.

Mucosal immunization schedule. Groups of mice (n=10) were bled one week prior to the first immunization. On days 1, 14, 28, and 42, mice were immunized intranasally with PBS, OVA (10 µg) alone, or OVA (10 µg) mixed with CT (1 µg), ML-I (1 µg), LEA (10 µg), PHA (10 µg), WGA (10 µg), or UEA-I (10 µg). In other examples, mice were immunized intranasally with 5 µg glycoprotein D2 (gD2) from Herpes simplex virus type 2 on days 1, 14, 28, and 49 alone or in an admixture with 1 µg of either CT, ML-I, ML-II, or ML-III. Mice were dosed with 30 µl of each preparation (15 µl per nostril) through fine tips attached to a pipette.

Collection of blood and mucosal secretions. Blood samples were collected one day prior to each immunization by bleeding from the tail vein following a 10 minute incubation at 37° C. Two weeks after the final immunization, animals were terminally anesthetized (hypnorin plus diazepam) to allow collection of salivary and vaginal secretions. Mice were then killed by anesthetic overdose followed by exsanguination. Blood was immediately collected and centrifuged, and the serum was stored at −20° C.

Absorbent cellulose wicks (Whatman International, UK) were used for collection of saliva and vaginal fluid as described previously (17). Wash fluid (ice-cold 0.01 M PBS, 50 mM EDTA, 5 mM PMSF, 5 µg/ml Aprotinin) was used for elution of antibody from wicks and for nasal and intestinal washes. Saliva was collected by the insertion of a wick tip into the mouth for 2 minutes (17). Antibody was extracted from wicks into 400 µl mucosal wash fluid. Vaginal fluid was collected by repeated flushing and aspiration of 50 µl wash fluid and insertion of a wick for 2 minutes. Antibody was extracted from wicks into 400 µl wash fluid. Nasotracheal washes were collected from decapitated animals by backflushing 0.5 ml of mucosal wash fluid from the trachea. Intestinal washes were obtained by flushing the small intestine with 10 ml of ice-cold wash fluid. All secretions were stored at −20° C. until required for analysis.

Detection of specific antibodies by ELISA. ELISAs were set up to enable measurement of specific IgG, IgA, and IgG subclasses to OVA, CT, and plant lectins. Sera (from 1:100) and mucosal secretions (from 1:2) were titrated in the appropriate dilution buffer. Microtiter plates (Immunolon 4, Dynatech) were coated with 75 µl of immunogen per well (1 µg/ml for CT/lectins, 50 µg/ml when measuring responses to OVA and 2 µg/ml when measuring responses to gD2) in carbonate-bicarbonate buffer, pH 9.6, and incubated at 4° C. overnight. After washing, plates were blocked with 2% gelatin/dilution buffer and incubated at 37° C. for 1 hour. Plates were washed, and samples were added, serially diluted, and incubated at 37° C. for 1 hour.

Biotinylated antiserum in dilution buffer was added and incubated at 37° C. for 1 hour. After further washes, ExtrAvidin® peroxidase (Sigma) diluted 1:750 in dilution buffer was added and incubated at 37° C. for 30 minutes. Plates were washed, and 50 µl/well of developing solution (TMB microwell peroxidase substrate (1-C), Kirkegaard and Perry Laboratories, Gaithersburg, Md.) was added. Plates were incubated in the dark with shaking at 37° C. for 30 minutes. The reaction was stopped by addition of 1M $H_2SO_4$, and the absorbance was read at 450 nm.

ELISA dilution buffers were as follows: CT (PBS+0.1% Tween (PBST)), OVA (PBST), WGA (100 mM N-acetylglucosamine/PBST), PHA (0.1% Fetuin/PBST), UEA-I (30 mM L-fucose/PBST), LEA (Chitin hydrolysate (1:200) (Vector)/PBST), ML-I (100 mM D-galactose/PBST). Working dilutions of anti-IgG (1:8000) and IgA (1:2600) biotinylated capture antisera (Sigma) were determined after preliminary assays with pre-immune and pooled positive sera. Working dilutions of IgG subclass antisera (Serotect) were as recommended by the manufacturers (IgG1 (1:4000), IgG2a (1:4000), IgG2b (1:2000), IgG3 (1:2000)). Endpoint titers were determined as the dilution of a serum or mucosal sample giving an OD value of 0.1 units greater than the mean of control samples at the same dilution.

Total IgA was quantified as specific IgA with the following modifications: plates were coated with goat anti-mouse IgA (1:8000; α-chain specific, Sigma), PBST was used as diluent, and 2% gelatin in PBST was used as blocking solution. Total IgA levels were calculated from the linear region of the IgA (IgA kappa, Sigma) standard curve. Total IgA endpoint titers were determined as the dilution of a sample giving an OD value of 0.1 units greater than buffer alone.

Statistics. Data are expressed as the mean±standard deviation. An unpaired two-tailed t-test was used to test for significance between groups. Where the standard deviations were significantly different between groups, a nonparametric test (Kruskal-Wallis test with Dunn's multiple comparison post test) was used to assess significance. Kruskal-Wallis nonparametric test with Dunn's multiple comparison post test was also used to assess significance of the total IgA data.

EXAMPLE 2

The Effect of Immunization on Total IgA Levels in Sera and Secretions

Mice were immunized by the intranasal route on days 1, 14, 28, and 42 with either PBS, OVA (10 µg) alone, or OVA (10 µg) together with CT (1 µg), ML-I (1 µg), LEA (10 µg), PHA (10 µg), WGA (10 µg) or UEA-I (10 µg). Samples were collected two weeks after the final immunization. The results are shown FIG. 1. Data represent the mean±SD.

After four intranasal immunizations with CT+OVA there was a significant increase in the concentration of total nasotracheal wash IgA ($p<0.01$) compared with all other groups. Co-administration of CT with OVA did not result in a significant rise in total IgA concentration in sera or the other mucosal secretions sampled. There was no significant effect of immunization with any of the plant lectins on total IgA levels in any of the secretions or in serum.

EXAMPLE 3

The Adjuvant Effect of Plant Lectins on OVA-specific Serum Antibody Responses

Mice were immunized intranasally on days 1, 14, 28, and 42 with either OVA (10 µg), alone or OVA (10 µg) together with CT (1 μg), ML-I (1 μg), LEA (10 μg), PHA (10 μg), WGA (10 μg) or UEA-I (10 μg). Sera were collected 1 day before each immunization and at the termination of the study. FIGS. 2A–D show the results of this experiment. Points refer to individual data, and the symbol (–) represents the mean titer.

Two weeks after a single immunization, OVA-specific serum IgG was detected in 5/10 mice immunized with CT+OVA and 1/10 mice immunized with ML-I+OVA but OVA-specific IgG was not detected in the other groups. After a second dose, higher responses were measured with detectable antibody in all mice immunized with CT+OVA (mean titer 40321) and in 9/10 mice immunized with ML-I+OVA (mean titer 11090). Of the other groups, specific IgG was only detected in mice immunized with UEA-I+OVA (mean titer 91).

After four doses, the highest mean IgG titers were in mice immunized with CT+OVA, being approximately 286-fold higher than in mice which received OVA alone. The mean titer in the group immunized with ML-I+OVA was approximately 118-fold higher than in mice which received OVA alone. Titers in mice immunized with PHA+OVA were similar to those in mice administered with OVA alone. Administration of LEA+OVA resulted in a small increase in mean titer compared with OVA alone (5-fold). Delivery of WGA and UEA-I with OVA respectively led to 41- and 51-fold increases in mean serum IgG anti-OVA titers compared with OVA alone.

In contrast to the groups which received CT+OVA and ML-I+OVA, responses in the groups immunized with WGA or UEA-I+OVA were highly variable. As a result, after the final dose only the CT+OVA and ML-I+OVA groups (difference not significant between groups) had mean OVA-specific IgG titers significantly higher (p<0.001) than the OVA only group. Titers in these groups were also significantly higher than in the PHA+OVA group (p<0.001).

In contrast to the high levels of specific IgG, very low titers of OVA-specific serum IgA were detected. In fact, after the final dose, significant levels of OVA-specific serum IgA were only detected in mice immunized with CT+OVA (mean titer, 220) and ML-I+OVA (mean titer, 80).

EXAMPLE 4

OVA-specific IgG Subclass Patterns

Figure 3:
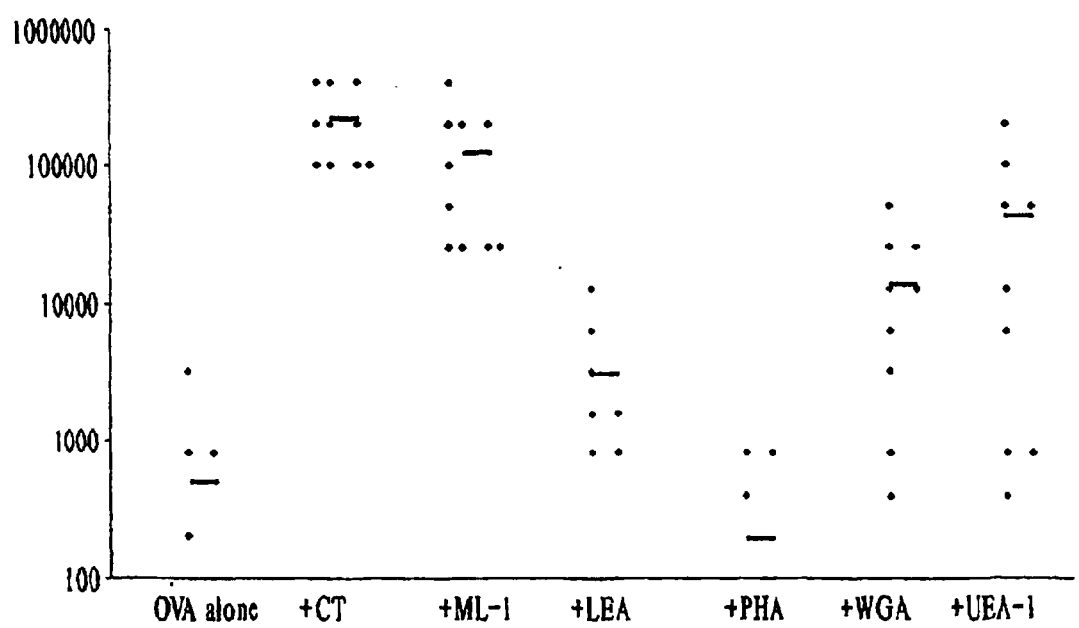
FIG. 3. Plot showing OVA-specific serum IgG1 antibody titers measured in mice immunized intranasally.
Figure 4A:
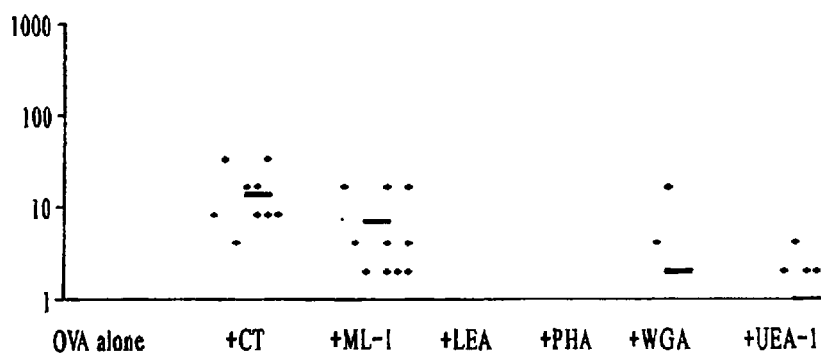
FIGS. 4A–D. Plots showing OVA-specific IgA antibody titers measured in secretions of mice immunized intranasally.
Figure 4B:
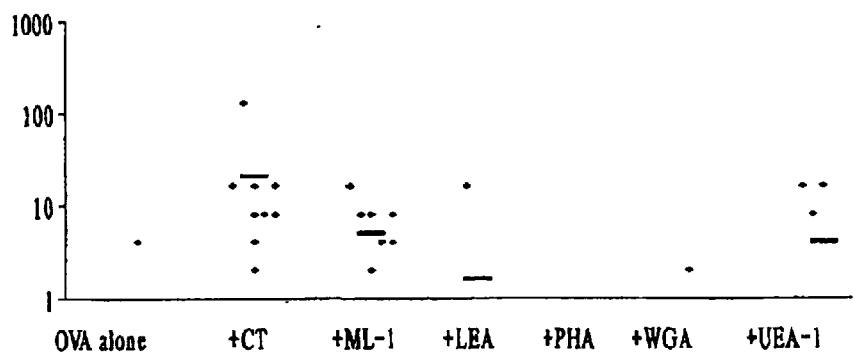
Figure 4C:
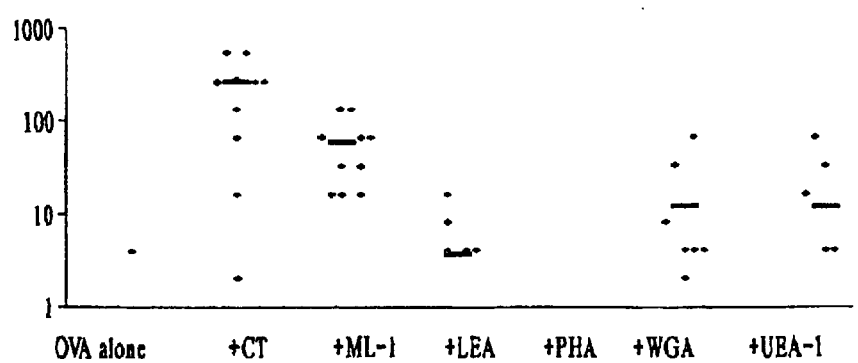
Figure 4D:
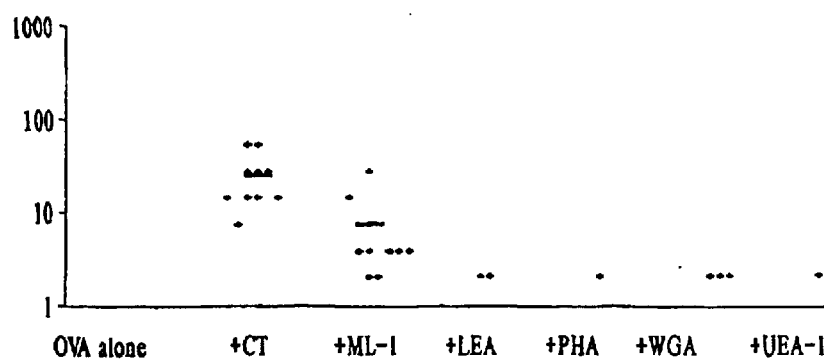
Figure 5A:
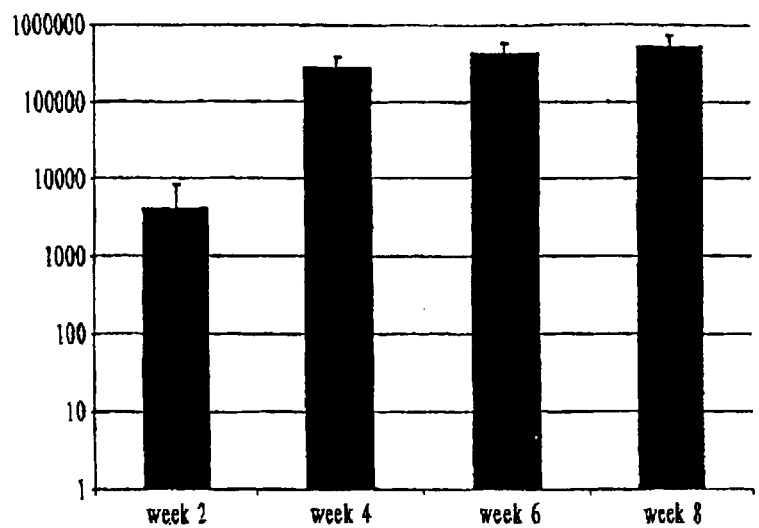
FIGS. 5A–F. CT/plant lectin-specific serum IgG antibody titers measured in mice immunized intranasally.
Figure 5B:
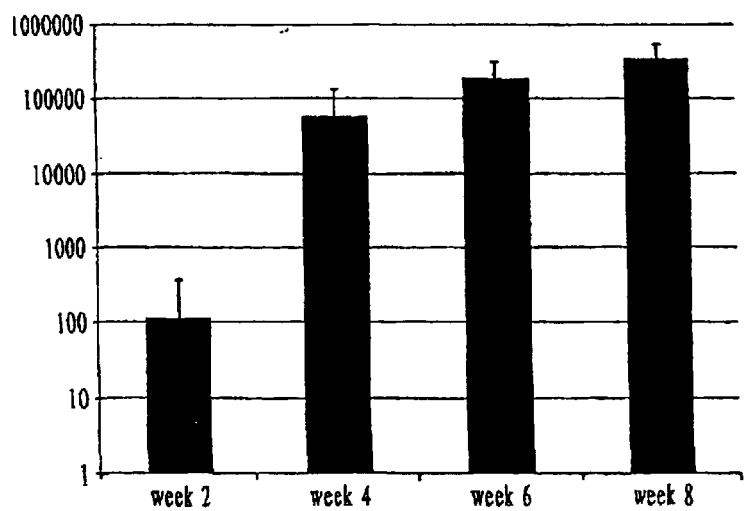
Figure 5C:
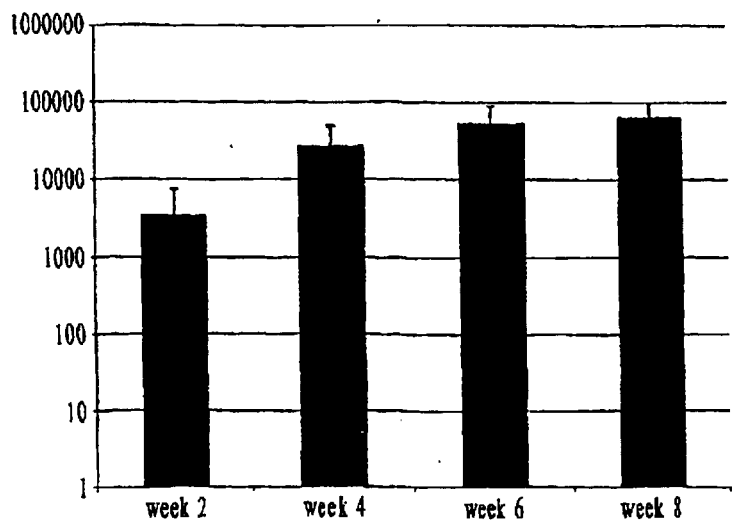
Figure 5D:
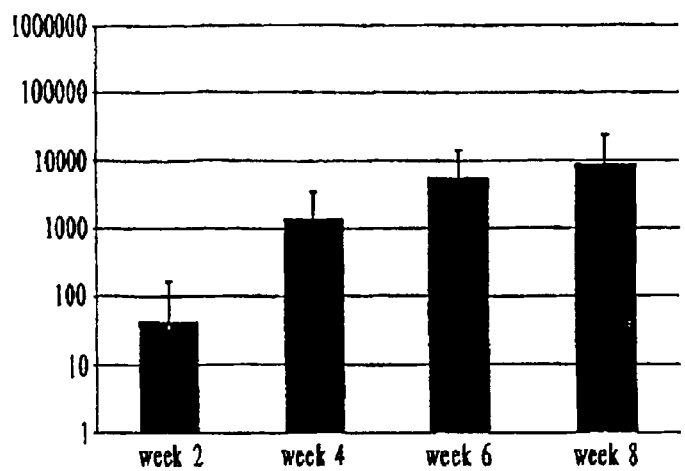
Figure 5E:
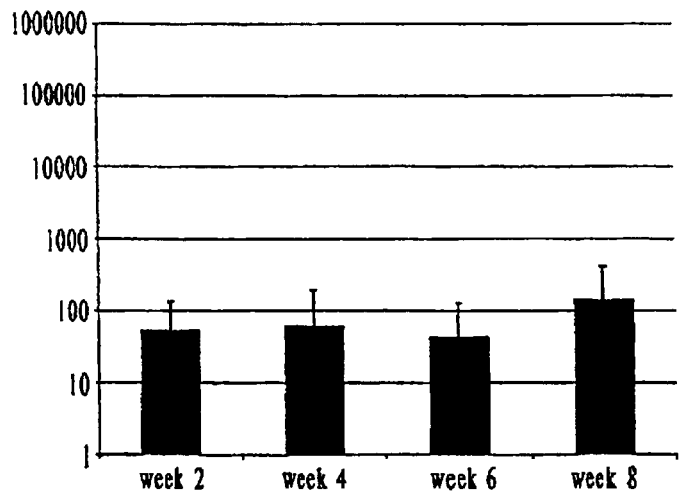
Figure 5F:
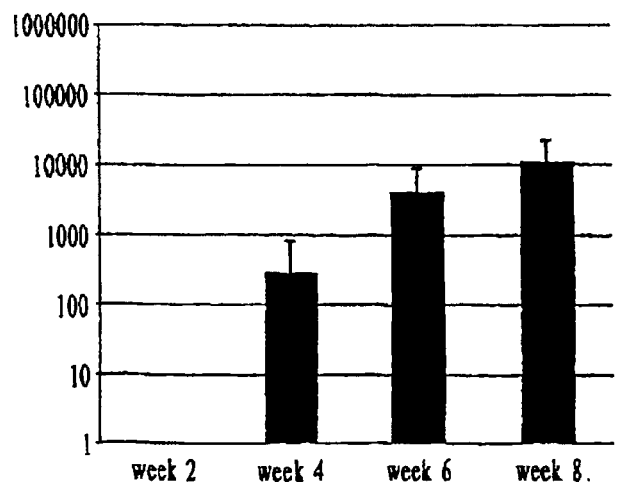
Figure 6A:
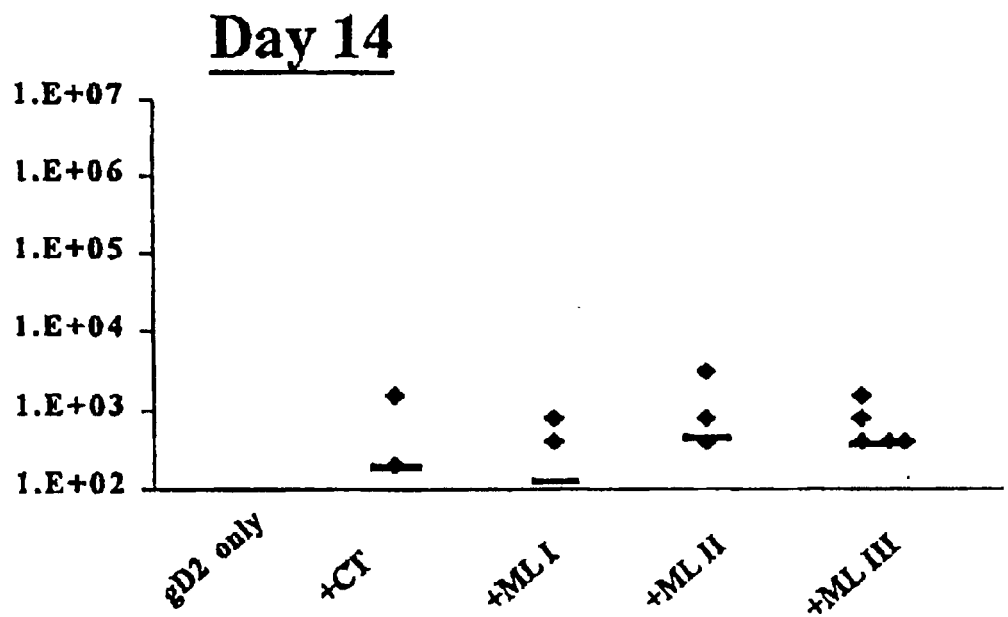
FIGS. 6A–D. Plots showing gD2-specific serum IgG antibody titers from mice immunized intranasally.
Figure 6B:
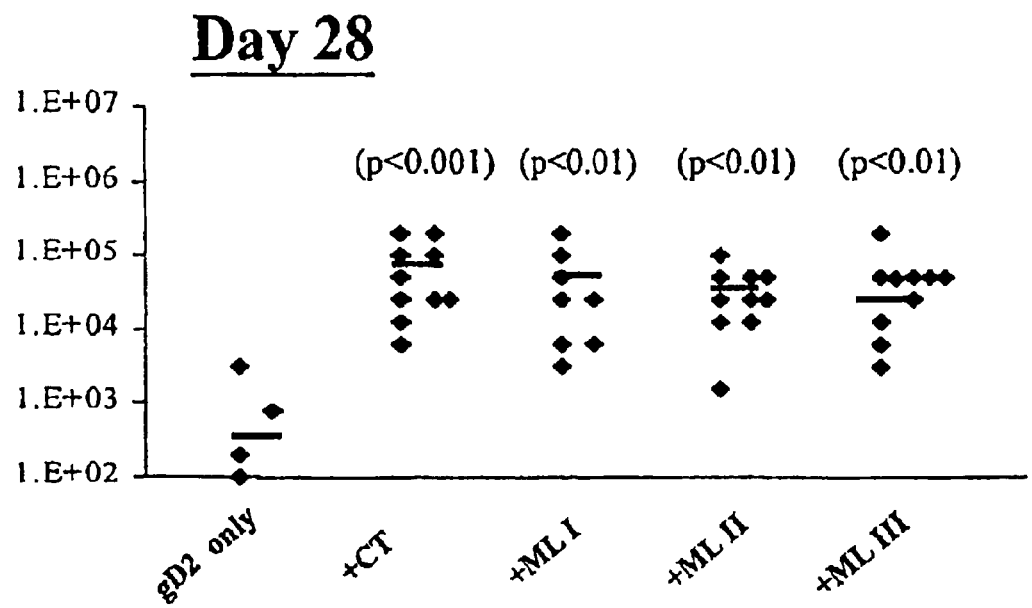
Figure 6C:
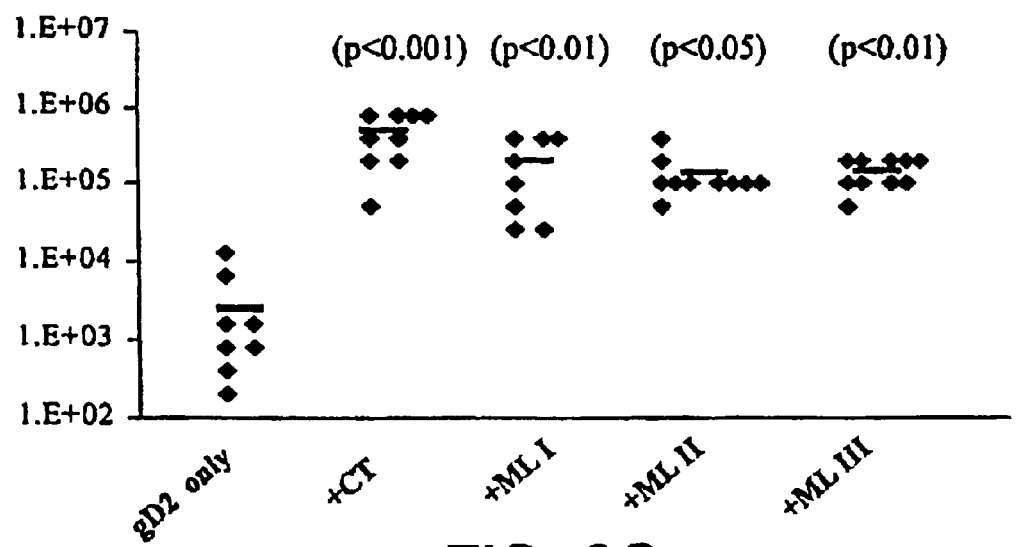
Figure 6D:
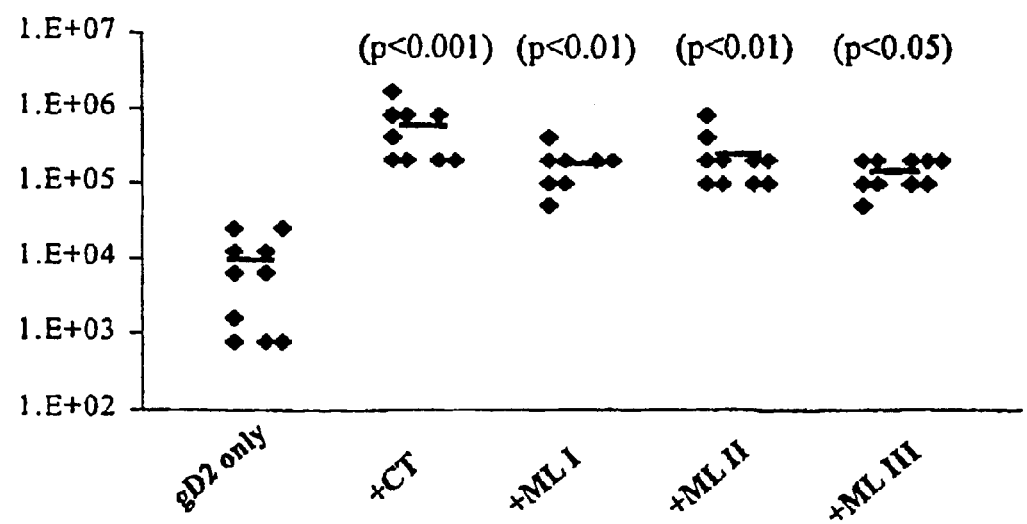

Mice were immunized intranasally on days 1, 14, 28, and 42 with OVA (10 μg) alone or OVA (10 μg) together with CT (1 μg), LEA, (1 μg), PHA (10 μg), WGA (10 μg), or UEA-I (10 μg). Samples were collected two weeks after the final immunization. FIG. 3 shows the results of this experiment. Points refer to individual data, and the symbol (–) represents the mean titer.

Analysis of the subclass profile of OVA-specific IgG antibodies indicated a very biased response. The IgG1 titers were similar to the titers of OVA-specific IgG in most groups. In mice immunized with CT+OVA and ML-I+OVA respectively, the mean titers were approximately 450-fold and 255-fold higher than in mice immunized with OVA alone. Titers in the CT+OVA group were significantly higher than in all groups except ML-I+OVA (p<0.05). Titers in the ML-I+OVA group were significantly higher than in groups which received OVA alone or PHA+OVA (p<001).

OVA-specific IgG2a was detected in 8/10 and 2/10 mice immunized with CT+OVA (mean titer 561) and ML-I+OVA (mean titer 331), respectively. Specific IgG2a was not detected in the other groups. Specific IgG2b was only detected in 2/10 mice immunized with CT+OVA and in none of the other groups. Specific IgG3 was not detected. These data are strikingly different to the CT-specific IgG isotype responses in these mice where relatively high titers of specific IgG2a and significant levels of IgG2b and IgG3 were detected (Table 1).

EXAMPLE 5

The Adjuvant Effect of Plant Lectins on OVA-specific Mucosal IgA Responses

Mice were immunized intranasally on days 1, 14, 28, and 42 with OVA (10 μg) alone or OVA (10 μg) together with CT (1 μg) ML-I (1 μg), LEA (10 μg), PHA (10 μg), WGA (10 μg), or UEA-I (10 μg). Titers were measured two weeks after the final immunization. The results are shown in FIGS. 4A–D. Points refer to individual data, and the symbol (–) represents the mean titer.

Specific IgA was detected at all mucosal sites sampled in mice immunized with CT+OVA and ML-I+OVA. There was no significant difference between the two groups. OVA-specific salivary IgA was not detected in mice immunized with OVA alone, LEA+OVA or PHA+OVA, but was detected in 2/10 and 4/10 mice immunized with WGA+OVA and UEA-I+OVA, respectively. In contrast, specific salivary IgA was measured in 9/10 and 10/10 mice immunized with CT+OVA and ML-I+OVA, respectively, with a two-fold higher mean titer in the CT+OVA group.

In vaginal washes, OVA-specific IgA was detected in 9/10 and 7/10 mice immunized with CT+OVA and ML-I+OVA, respectively. The mean titer was four-fold higher in the CT+OVA group, but this was largely the result of one high responder. OVA-specific vaginal wash IgA was not detected in mice immunized with PHA+OVA and was detected in 1/10 mice immunized with either OVA alone, LEA+OVA, or WGA+OVA, and in 3/10 mice immunized with UEA-I+OVA.

High titers of OVA-specific IgA were detected in nasotracheal washes from all mice immunized with CT+OVA or ML-I+OVA, with approximately a five-fold higher titer in the CT+OVA group. OVA-specific nasotracheal wash IgA titers were significantly higher (p<0.05) in mice immunized with CT+OVA than in all groups except ML-I+OVA.

Remarkably, the OVA-specific nasotracheal wash IgA titers in these groups were comparable to the serum IgA titers. Total IgA titers in sera from mice immunized with CT+OVA and ML-I+OVA were 33-fold and 73-fold higher than in nasotracheal washes, respectively. Specific IgA was detected in the nasotracheal washes of 1/10 mice immunized with OVA alone but not in any mice immunized with PHA+OVA. OVA-specific nasotracheal wash IgA was measured in 7/10 mice immunized with WGA+OVA and 5/10 mice immunized with UEA-I+OVA or LEA+OVA, respectively.

OVA-specific IgA was detected in gut washes from all mice immunized with CT+OVA or ML-I+OVA, with approximately a four-fold higher titer in the CT+OVA group.

Titers in these groups were not significantly different from each other but were significantly higher (p<0.05) than in all other groups. Among the other groups, OVA-specific gut wash IgA was only detected sporadically at a maximum titer of 1:2.

EXAMPLE 6

CT/Plant Lectin-specific Responses

Mice were immunized intranasally on days 1, 14, 28, and 42 with OVA (10 μg) together with CT (1 μg), ML-I (1 μg), LEA (10 μg), PHA (10 μg), WGA (10 μg) or UEA-I (10 μg). The results are shown in FIGS. 5A–F. Data are presented as the mean±SD. Data are titers of specific serum IgG measured two weeks after the final dose of immunogen.

CT-specific serum IgG was detected in all animals after a single dose of CT+OVA, and titers increased with each subsequent dose. Specific antibodies of all four IgG subclasses were detected in sera after four doses (Table 1). The highest titers were of IgG1, although CT-specific IgG2a, IgG2b and IgG3 were also detected. After the final dose, CT-specific serum IgA was detected in all mice, with a mean titer of 4481.

Specific IgA was also detected in all animals in saliva, vaginal wash, nasotracheal wash, and gut wash. Salivary IgA titers were relatively consistent between animals (approximately 10-fold lower mean titer than in serum). Total IgA titers in saliva from these mice were 1340-fold lower than in serum. Vaginal IgA titers were highly variable, with a single high responder increasing the mean titer. High titers of CT-specific IgA were measured in nasotracheal washes from all animals with a mean titer comparable to the serum IgA titer. Specific IgA was also detected in intestinal washes of all mice, but at a lower mean titer than at the other mucosal sites sampled.

Intranasal delivery of a single dose of ML-I+OVA stimulated the production of ML-I specific IgG in 3/10 mice. After the second and subsequent doses, high titers of specific IgG were detected in all mice (FIG. 5). Analysis of ML-I-specific serum IgG subclasses found high titers of ML-I-specific IgG1 (Table 1). ML-I-specific IgG2a and IgG2b were also detected, but specific IgG3 was not detected. ML-I-specific IgA was detected in all mice in serum and at all mucosal sites sampled after four doses. Titers in the saliva were consistent for all animals, while a single very high responder increased the mean titer in the vaginal washes. High ML-I-specific IgA titers were measured in nasotracheal washes of all animals. As with CT, the mean ML-I-specific titer in nasotracheal washes was comparable with the serum IgA titer (approximately two-fold lower), which was remarkable as the total IgA titers in nasotracheal washes were 73-fold lower than in sera from these mice. Specific IgA was also detected in gut washes from all animals.

In mice immunized with LEA+OVA, LEA-specific serum IgG was detected in 9/10 mice after a single dose. The titer increased after each subsequent does to a relatively high level after the final immunization (FIG. 5). Analysis of IgG subclasses found high titers of LEA-specific IgG1 and a low mean IgG2a titer (Table 1). Specific serum IgA was detected in 7/10 mice after four doses, but at a low level. Specific IgA was also detected in all four mucosal secretions tested, although in comparison to the data in the CT+OVA and ML-I+OVA groups the titers were highly variable.

PHA-specific serum IgG was detected in 1/10 mice after a single dose of PHA+OVA. After subsequent doses the titer increased, and specific IgG was present in 8/10 animals after the final dose (FIG. 5). Of the IgG subclasses, only specific IgG1 was detected (Table 1). Low titers of specific serum IgA were detected in all animals. PHA-specific IgA was not detected in saliva or vaginal washes but was detected in nasotracheal washes of 5/10 mice and gut washes of 1/10 mice.

The lowest titers of specific antibody were elicited to WGA, even after four doses of WGA+OVA (FIG. 5). Specific IgG1 was detected in 2/10 mice, and the other IgG subclasses were not detected (Table 1). Specific IgA was detected in a number of mice after four doses, but at a maximum titer of 1:100. Low titers of specific IgA were measured in a small number of mice in saliva, vaginal washes, and nasotracheal washes. These data are in contrast to the OVA-specific data from this group, where relatively high levels of OVA-specific serum IgG were detected in a number of mice.

UEA-I-specific serum IgG was not detected after a single dose of UEA-I+OVA, but was detected after subsequent doses and in 8/10 mice after the final dose (FIG. 5). Specific IgG1 was detected in 9/10 mice after the final dose (Table 1), specific IgG2a in 1/10 mice, and IgG2b and IgG3 were not detected. Specific serum IgA was detected in 3/10 mice after the final dose. Relatively low levels of IgA were detected in saliva, vaginal washes, and nasotracheal washes.

The present data indicates that the type of response elicited to the adjuvant and to the immunogen may differ. High titers of specific IgG1 were detected to both OVA and CT, but while relatively high titers of CT-specific IgG2a were measured, there was little or no OVA-specific IgG2a. Delivery of ML-I+OVA led to similar results, although the ML-I-specific IgG2a titers were relatively low. Previous work found higher OVA-specific IgG1 than IgG2a titers after delivery of OVA+CT, while higher titers of CT-specific IgG2a than IgG1 were found in the same mice (24). Feeding mice with CT+keyhole limpet hemocyanin (KLH) stimulated a strong KLH-specific secretory IgA response in mice which were high responders to CT with a much smaller effect in poor responders (29). Thus, the oral adjuvant effect of CT depended on a strong immune response to CT itself. However, WGA and UEA-I increased the serum IgG response to OVA (through not significantly) and were not highly immunogenic. A recent study found that several dietary lectins, including PHA, could trigger human basophils to release IL-4 and IL-13. ConA and PHA-E, for example, induced IL-4 levels as high as those obtained by stimulation with anti-IgE antibodies. Lectins that stimulated high levels of IL-4 also triggered release of IL-13 and histamine, possibly by inducing IL-4, which is required to switch towards a Th2-type response (30).

Despite the induction of high serum IgG titers to OVA in mice immunized with CT or ML-I+OVA, serum IgA was barely detectable. Previous work found that immunogen-specific serum IgA was not detected in mice after two intranasal immunizations with *V. cholerae zot* protein or LT+OVA (19). Similarly, it was found that oral delivery of LT+TT stimulated high levels of serum IgG antibodies to TT, while anti-TT serum IgA was not detected (23). While both CT and ML-I effectively stimulated anti-OVA IgA in all mucosal secretions, the levels were highest in nasotracheal washes and saliva. Because the total serum IgA titers in mice immunized with CT+OVA and ML-I+OVA were 33-fold and 73-fold higher than in nasotracheal washes and 1340-fold and 1176-fold higher than in saliva, respectively, the OVA-specific IgA titers at these sites indicate the induction of local responses. Antibody titers in vaginal washes were highly variable, which may reflect hormonal influences (31).

Figure 7A:
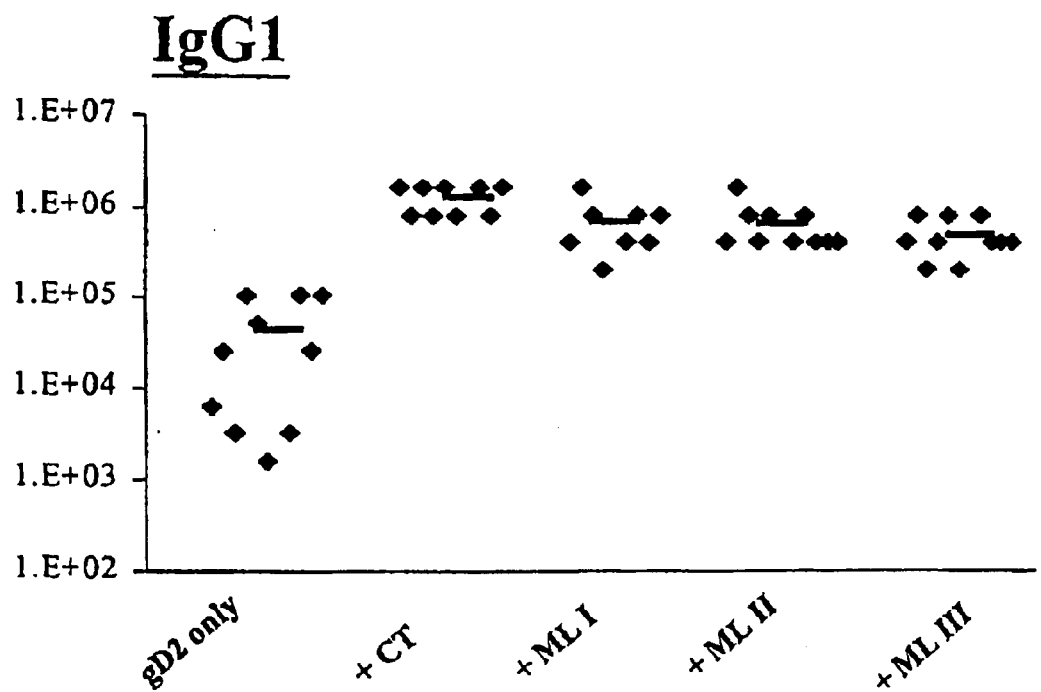
FIGS. 7A–D. Plots showing gD2-specific serum IgG subclass antibody titers.
Figure 7B:
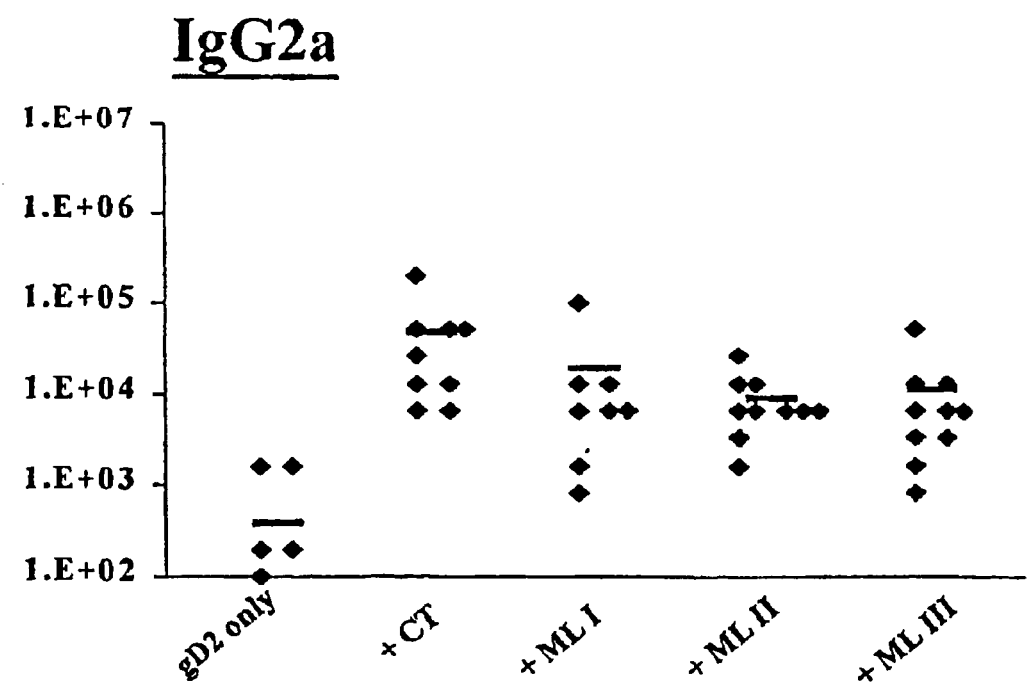
Figure 7C:
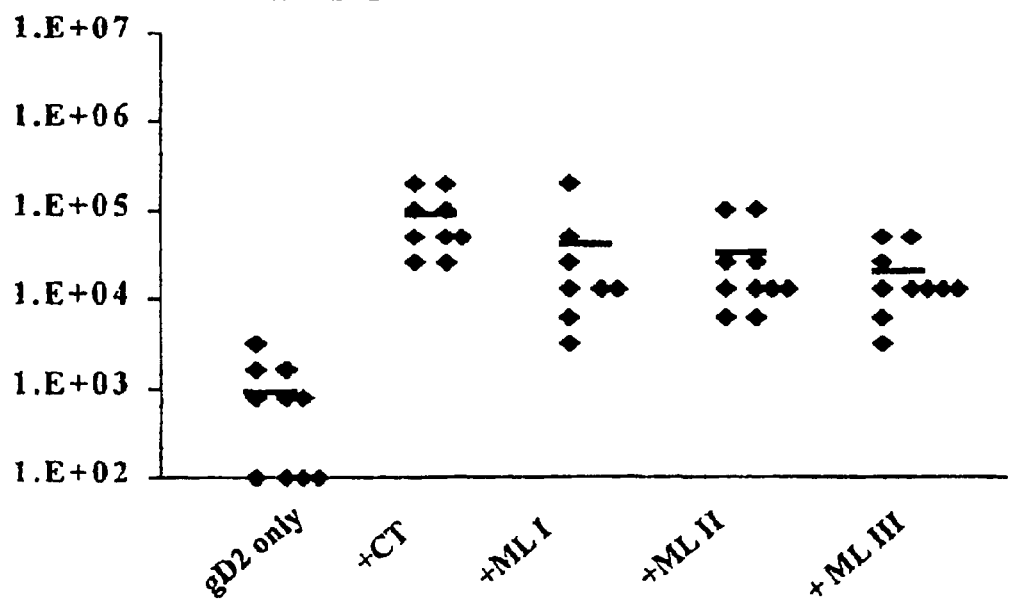
Figure 7D:
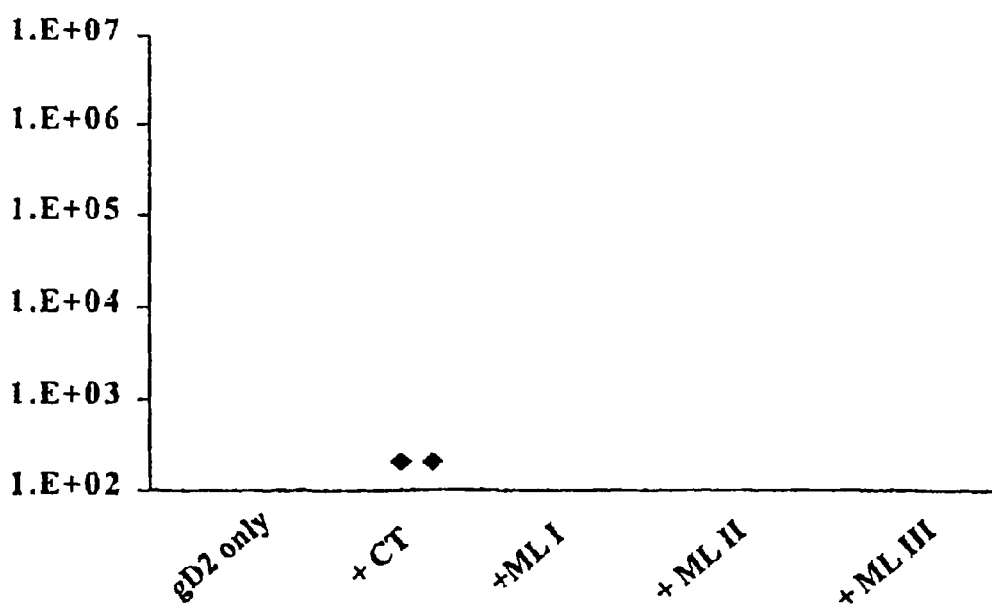

CT (1 μg), ML-I (1 μg), ML-II (1 μg), or ML-III (1 μg). Samples were collected two weeks after the final immunization. Data are titers measured two weeks after the final immunization. FIG. 7A, IgG1; FIG. 7B, IgG2a; FIG. 7C, IgG2b; FIG. 7D, IgG3. Points refer to individual data and the symbol (−) represents the mean titer. p values in parentheses refer to significance of data compared with the gD2 only group.

Titers of serum-specific IgG1, IgG2a, and IgG2b antibodies were increased in the mice treated with each of the three mistletoe lectins.

TABLE 1

| Antigen | Serum IgG and IgG subclass titer | | | | | IgA titer | | | | |
|---|---|---|---|---|---|---|---|---|---|---|
| | IgG | IgG1 | IgG2a | IgG2b | IgG3 | Serum | saliva | vagina | nasal | gut |
| CT | 532481 | 339841 | 83201 | 3681 | 1201 | 4481 | 409.6 | 358.8 | 3200 | 211.2 |
| ML-I | 337961 | 409601 | 2881 | 901 | — | 1841 | 64 | 440.3 | 819.2 | 33.6 |
| LEA | 61441 | 78081 | 361 | 11 | — | 361 | 11 | 10.2 | 49.6 | 5.2 |
| PHA | 8561 | 7161 | — | — | — | 211 | — | — | 4.6 | 0.2 |
| WGA | 141 | 21 | — | — | — | 51 | 0.2 | 0.6 | 1.4 | — |
| UEA-I | 10881 | 18441 | 11 | — | — | 31 | 1.8 | 1 | 5 | — |

EXAMPLE 7

Three Different Lectins from the European Mistletoe (*Viscum album*), ML-I, ML-II, and ML-III, Increase the Titers of gD2-Specific Serum IgG Antibodies after Intranasal Administration One microgram of each of these three lectins was admixed with 5 μg glycoprotein D2 (gD2) from Herpes simplex virus type 2 and delivered intranasally to mice on days 1, 14, 28, and 49, as described above. Other mice were immunized intranasally with 5 μg gD2 alone or with 5 μg gD2 admixed with 1 μg CT. Sera were collected 1 day before each immunization and at the termination of the study. Titers of gD2-specific serum IgG antibodies were measured as described above.

The results are shown in FIGS. 6A–D. Points refer to individual data, and the symbol (−) represents the mean titer. Each of the three mistletoe lectins exhibited adjuvant activity comparable to that exhibited by CT.

EXAMPLE 8

Increases in the Titers of gD2-Specific Serum IgG Subclass Antibodies after Intranasal Administration Mice were immunized intranasally on days 1, 14, 35, and 49 with either gD2 alone (5 μg) or gD2 (5 μg) together with

EXAMPLE 9

Figure 8A:
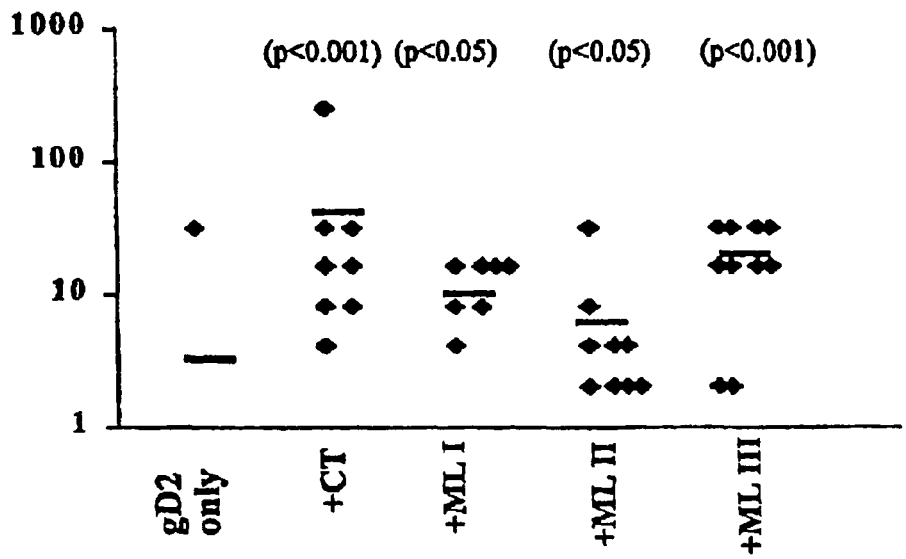
FIGS. 8A–D. Plots showing gD2-specific IgA antibody titers measured in secretions.
Figure 8B:
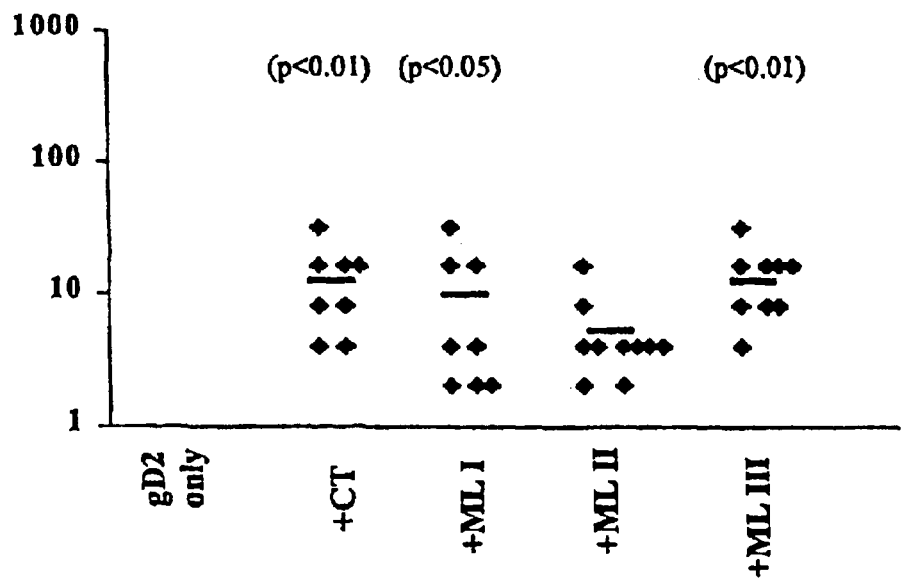
Figure 8C:
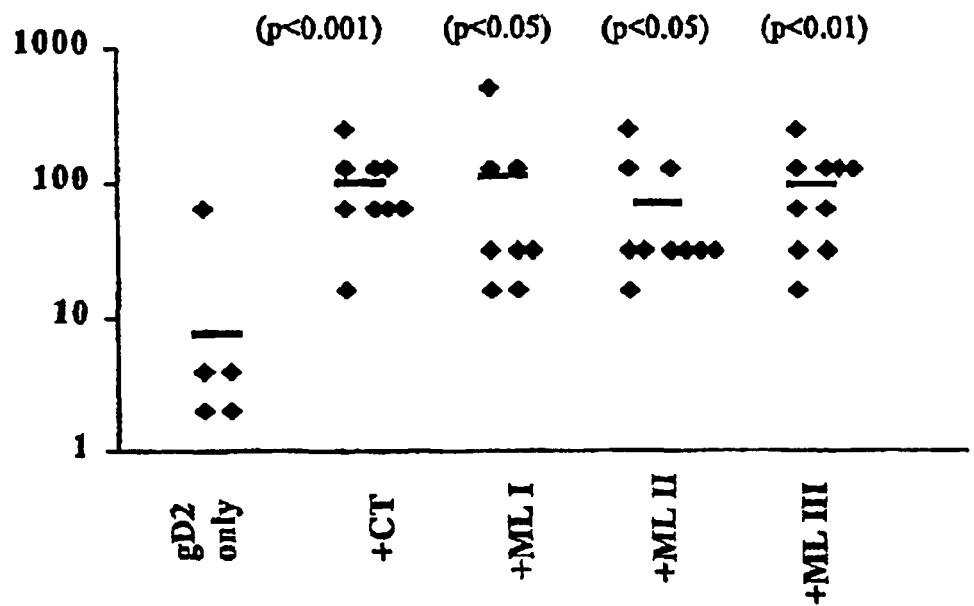
Figure 8D:
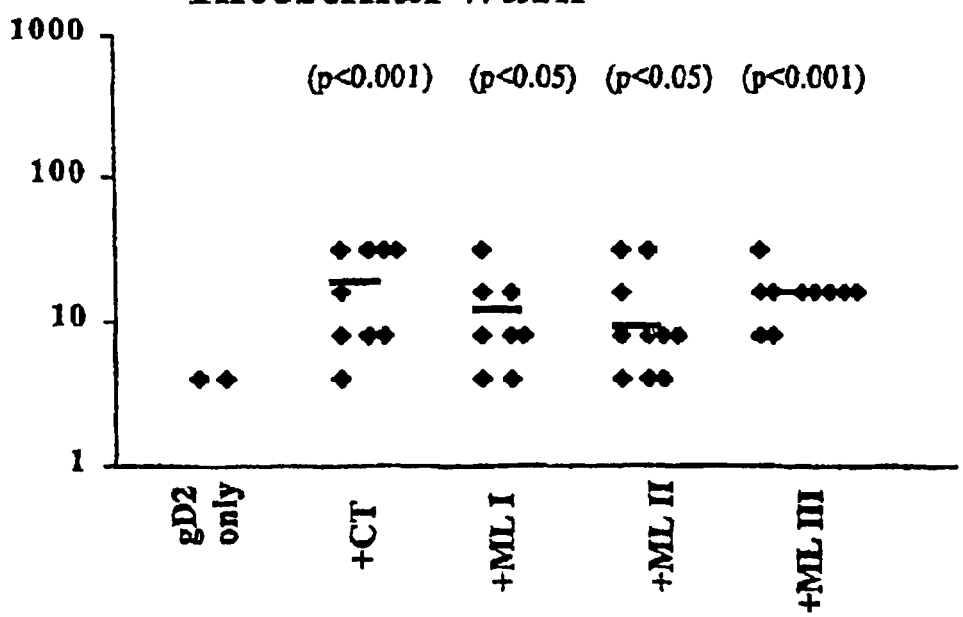
Figure 9A:
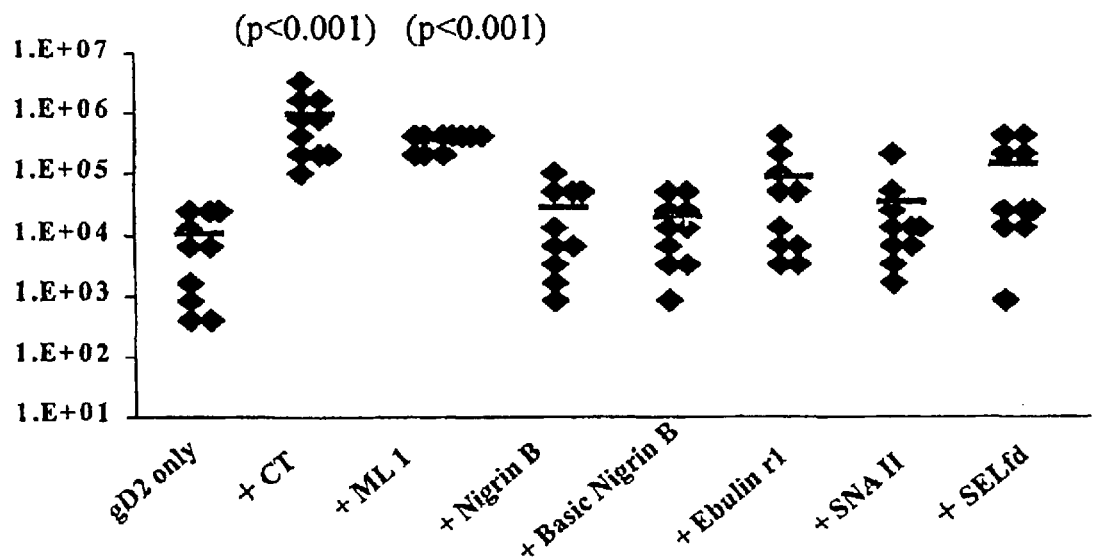
FIG. 9A, IgG.
Figure 9B:
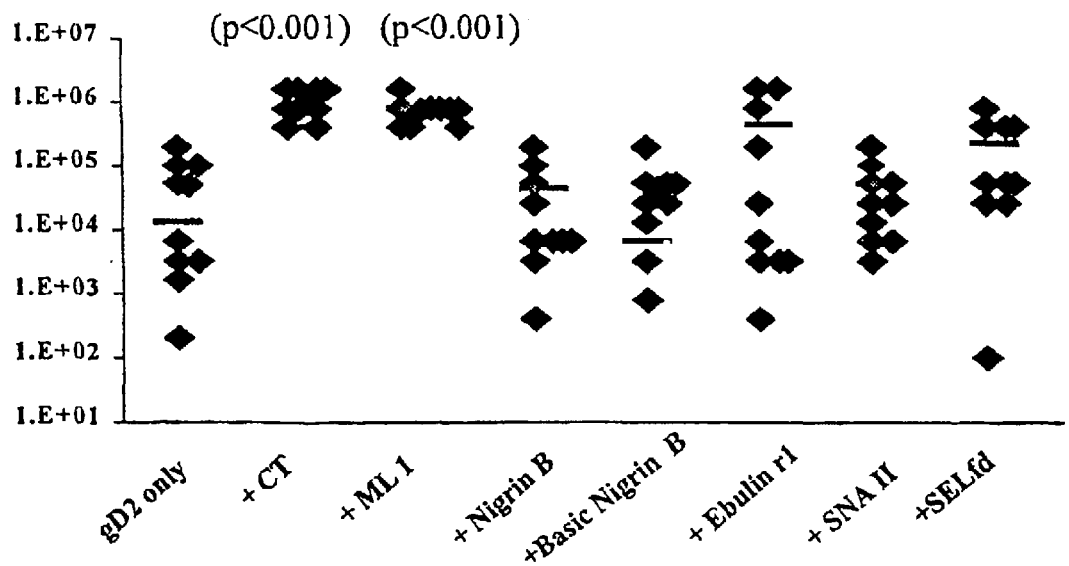
FIG. 9B, IgG1.
Figure 9C:
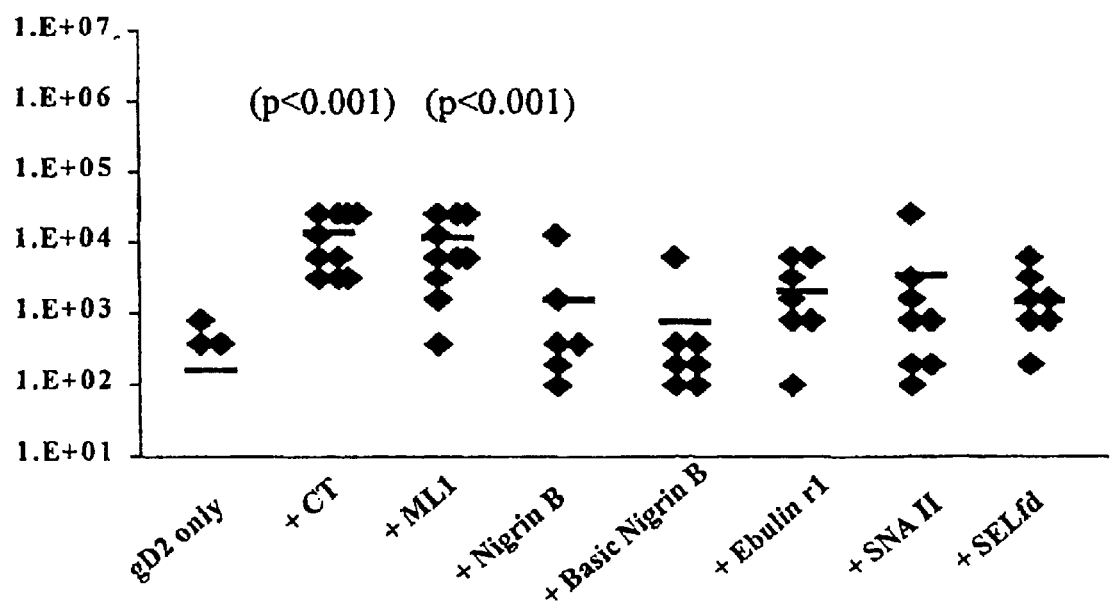
Figure 9D:
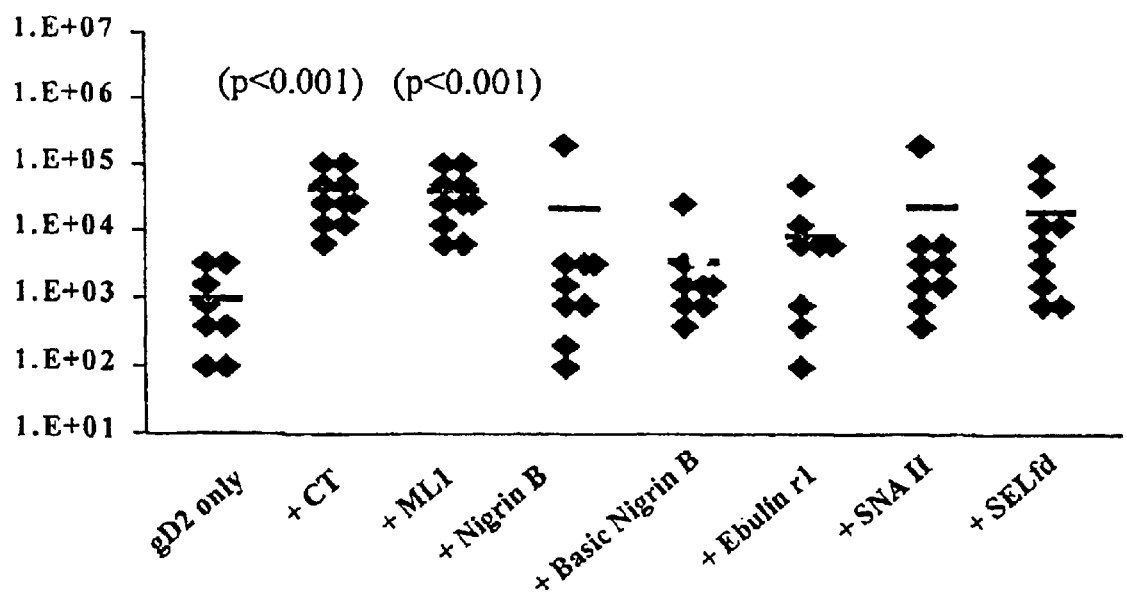
FIG. 9D, IgG2b.
Figure 10A:
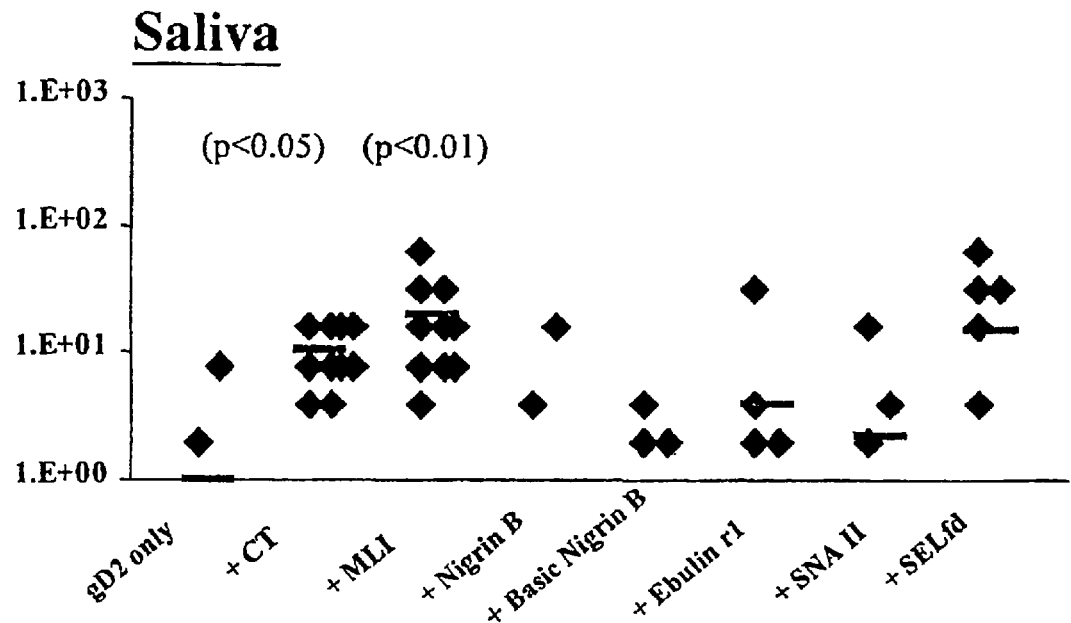
FIG. 10A, saliva.
Figure 10B:
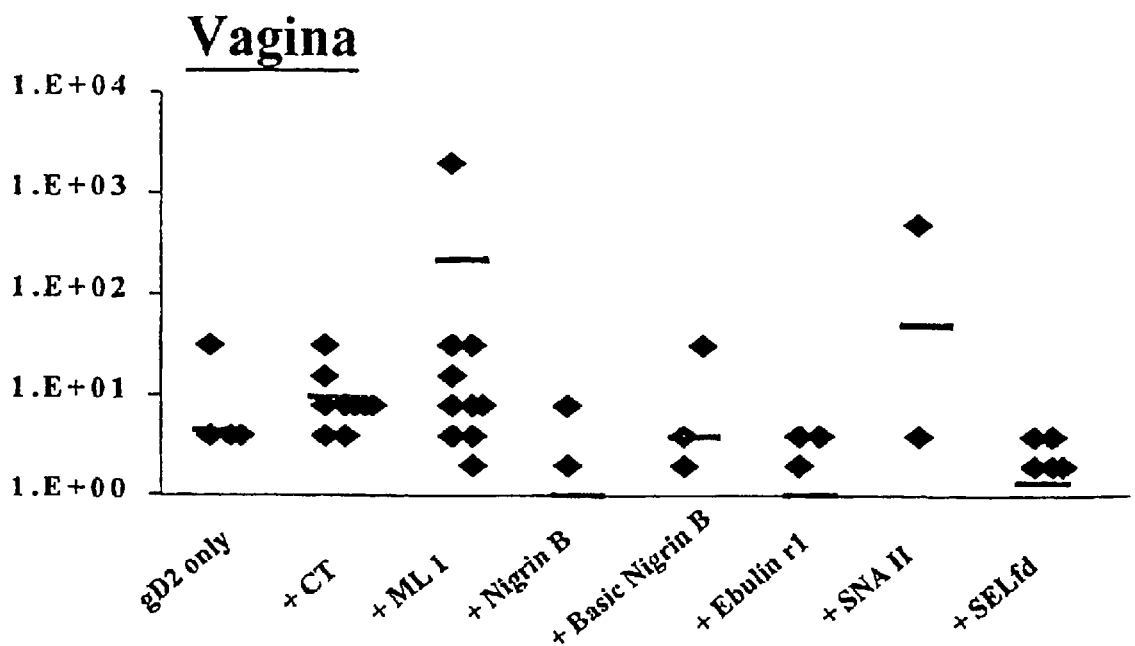
FIG. 10B, vaginal wash.
Figure 10C:
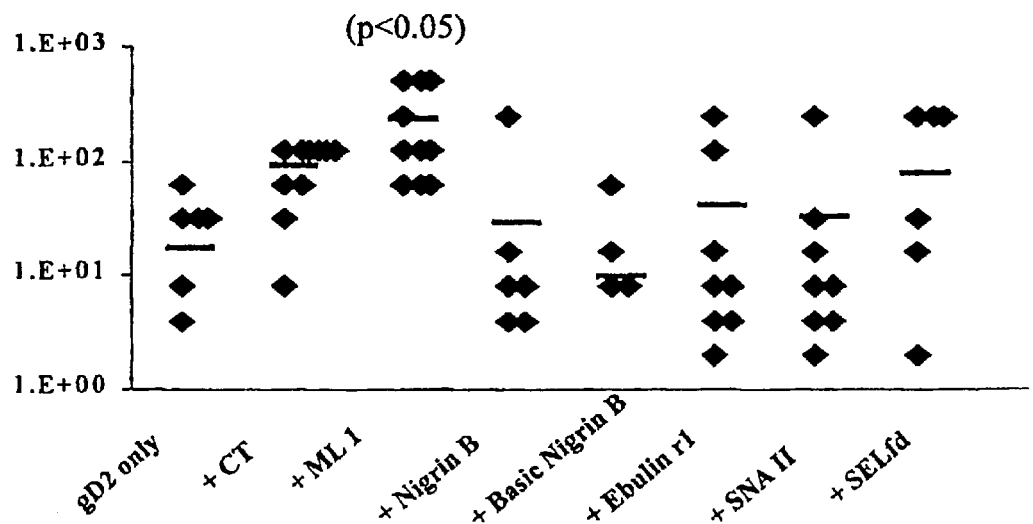
FIG. 10C, nasotracheal wash.
Figure 10D:
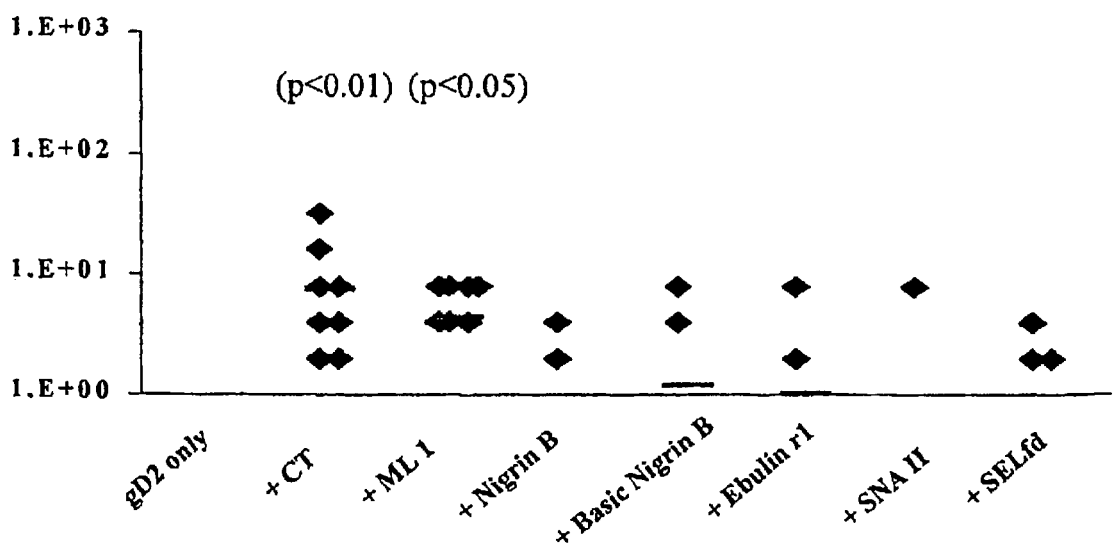
FIG. 10D, gut wash.

ML-I, ML-II, and ML-III Increase gD2-Specific IgA Antibodies Titers in Mice after Intranasal Immunization gD2-specific IgA antibody titers were measured in secretions of mice immunized intranasally on days 1, 14, 35 and 49 with gD2 (5 μg) alone or gD2 (5 μg) together with CT (1 μg), ML-I (1 μg), ML-II (1 μg) or ML-III (1 μg). Data are titers measured two weeks after the final immunization in FIG. 8. FIG. 8A, saliva; FIG. 8B, vaginal wash; FIG. 8C, nasotracheal wash; FIG. 8D, intestinal wash. Points refer to individual data and the symbol (−) represents the mean titer. p values in parentheses refer to significance of data compared with the gD2 only group.

Each of the mistletoe lectins increased the titers of gD2-specific IgA antibodies in each of the secretions tested.

Table 2 shows lectin-specific antibody responses in mice immunized intransally with gD2 (5 μg), alone or together with CT/plant lectins (1 μg). Mice (n=10) were immunized on days 0, 14, 28, and 42, and samples were collected on days 56 and 57.

TABLE 2

| Lectin/toxin | Serum IgG and IgG subclass titer | | | | | IgA titer | | | | |
|---|---|---|---|---|---|---|---|---|---|---|
| | IgG | IgG1 | IgG2a | IgG2b | IgG3 | Serum | Saliva | Vagina | nasal | gut |
| ML-I | 313600 | 742400 | 2200 | 18400 | — | 2700 | 53 | 84 | 432 | 6 |
| ML II | 655360 | 655360 | 3040 | 23040 | — | 520 | 98 | 34 | 166 | 30 |
| ML III | 179200 | 327680 | 1220 | 9920 | — | 520 | 58 | 88 | 113 | 7 |
| CT | 523378 | 568889 | 176356 | 193422 | 211 | 7111 | 484 | 409 | 1771 | 53 |

EXAMPLE 10

Mucosal Immunogenicity and Adjuvanticity of Nontoxic Type II RIPs and Related Molecules The mucosal (intranasal) immunogenicity and adjuvanticity of nontoxic type II RIP (Nigrin B, Basic Nigrin B, Ebulin r1) and molecules related to their B subunits (SNA II, SELfd) was compared with that of ML-1 and CT. Mice were immunized intranasally with gD2 (5 µg) alone or together with plant lectins or cholera toxin (CT) (1 µg). Mice were immunized on days 0, 21, and 42 and samples were collected on days 56 and 57. Lectin-specific responses and responses to the bystander antigen, gD2, were measured by ELISA.

FIG. 9 shows the gD2-specific total serum IgG and IgG subclass titers from mice immunized intranasally on days 1, 21, and 92 with either gD2 (5 µg) alone or gD2 (5 µg) together with 1 µg of CT, ML-I, Nigrin B, Basic Nigrin B, Ebulin r1, SNA II or SELfd. Sera were collected at the termination of the study. Points refer to individual data and the symbol (−) represents the mean titer. p values in parentheses refer to significance of data compared with the gD2 only group.

FIG. 10 shows gD2-specific IgA antibody titers measured in secretions of mice immunized intranasally on days 1, 21, and 42 with either gD2 (5 µg) alone or gD2 (5 µg) together with 1 µg of CT, ML-I, Nigrin B, Basic Nigrin B, Ebulin r1, SNA II or SELfd. Data are titers measured two weeks after the final immunization in (a) saliva, (b) vaginal wash, (c) nasotracheal wash, (d) intestinal wash. Points refer to individual data and the symbol (−) represents the mean titer. p values in parentheses refer to significance of data compared with the gD2 only group.

Table 3 shows the immunogenicity of type II RIP and related molecules. Antibody responses were measured in mice immunized intranasally with gD2 (5 µg) alone or together with CT/lectins (1 µg). Groups of mice (n=10) were immunized on days 0, 14, 28 and 42 and samples were collected on days 56 and 57.

Figure 11A:
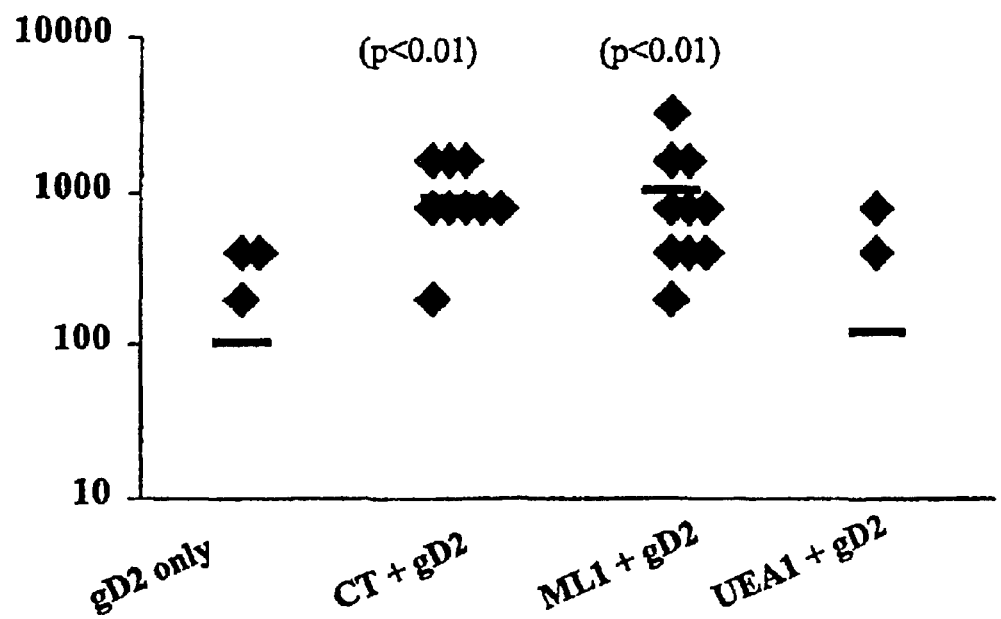
FIG. 11A, serum IgA.
Figure 11B:
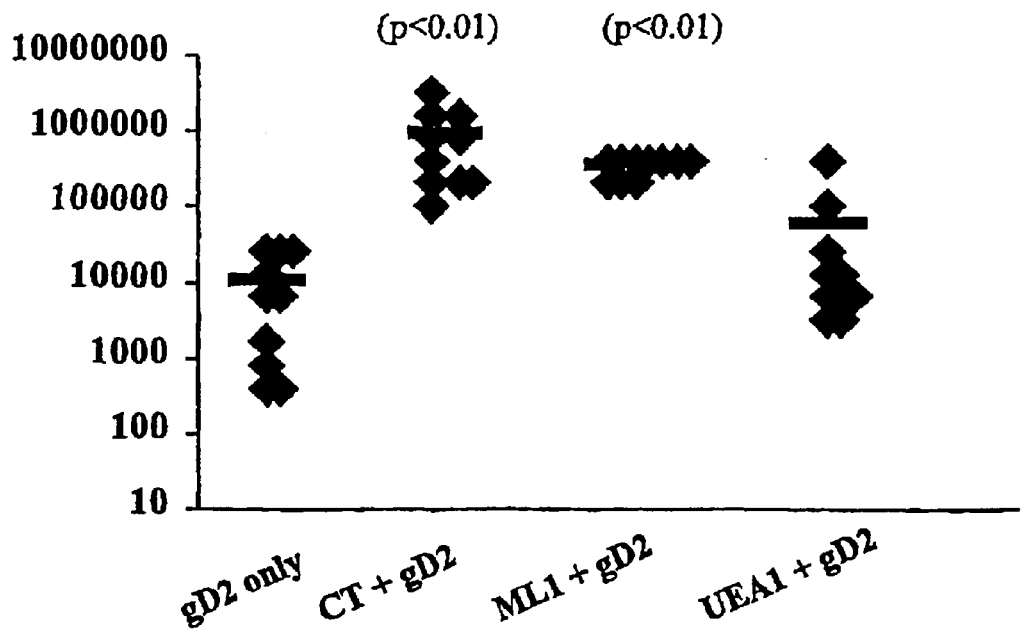
FIG. 11B, serum IgG.

FIG. 11 shows gD2-specific serum IgA and IgG antibody titers measured in mice immunized intranasally on days 1, 21, and 42 with either gD2 (5 µg) alone or gD2 (5 µg) together with 1 µg of CT, ML-I, or UEA-1. Data are titers measured two weeks after the final immunization. Points refer to individual data and the symbol (−) represents the mean titer. p values in parentheses refer to significance of data compared with the gD2 only group.

Figure 12A:
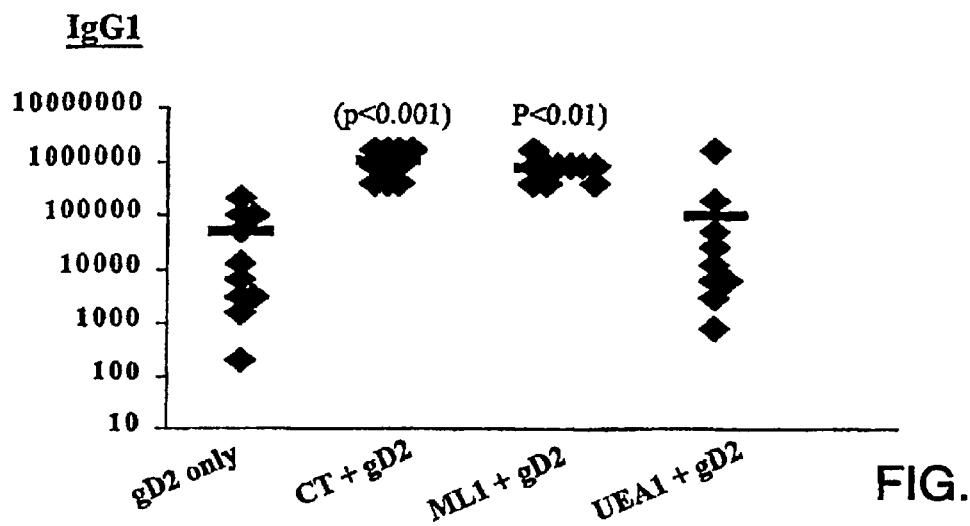
FIG. 12A, IgG1.
Figure 12B:
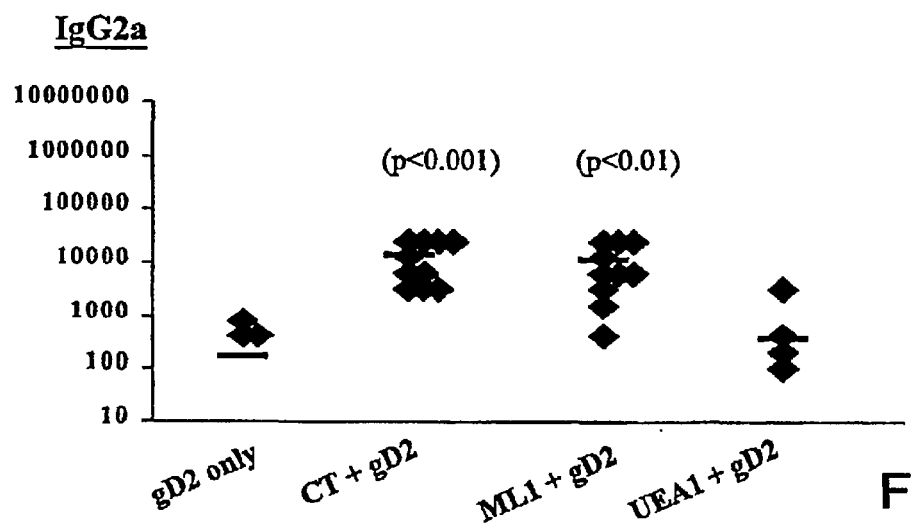
Figure 12C:
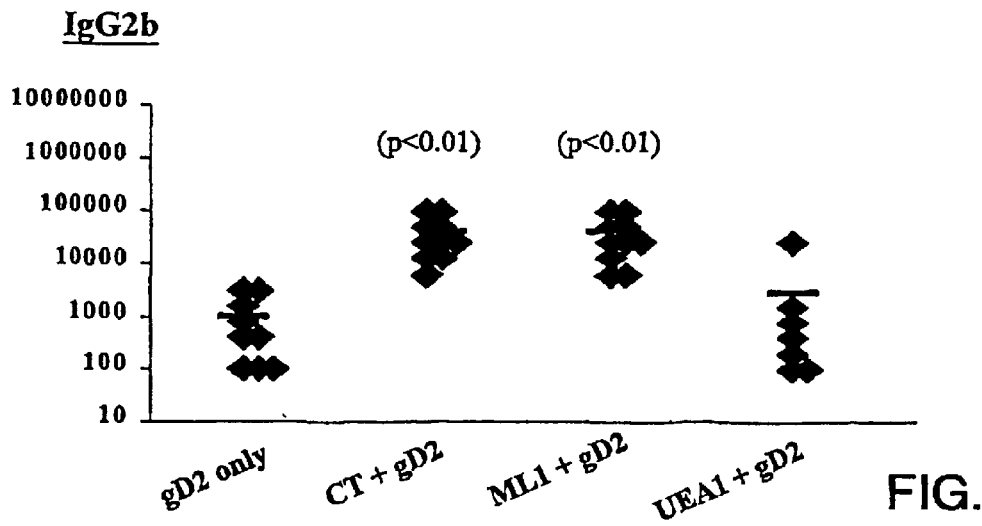
FIG. 12C, IgG2b.
Figure 13A:
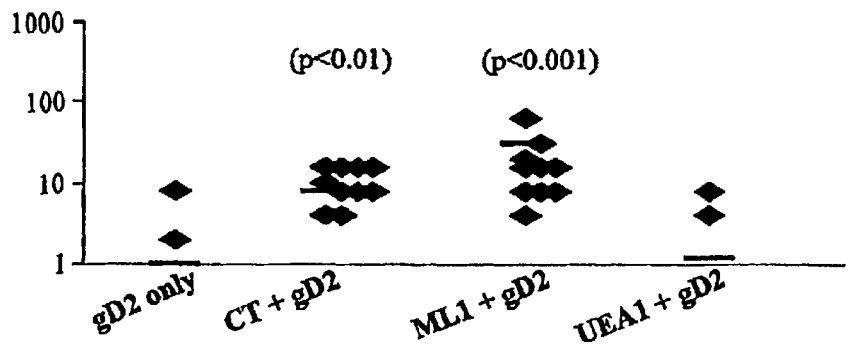
FIG. 13A, saliva.
Figure 13B:
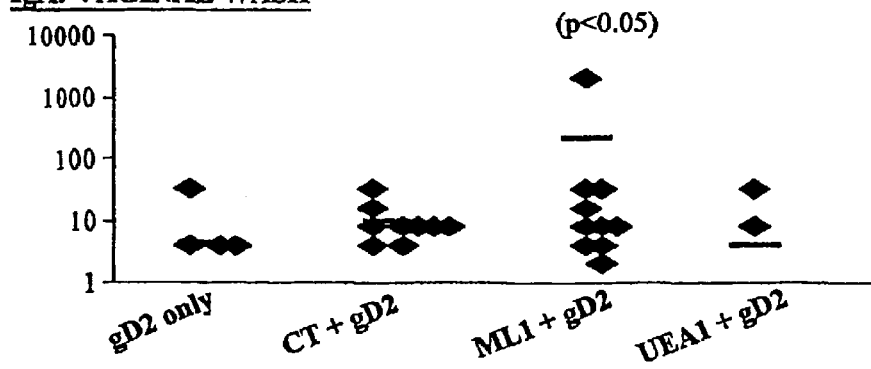
FIG. 13B, vaginal wash.
Figure 13C:
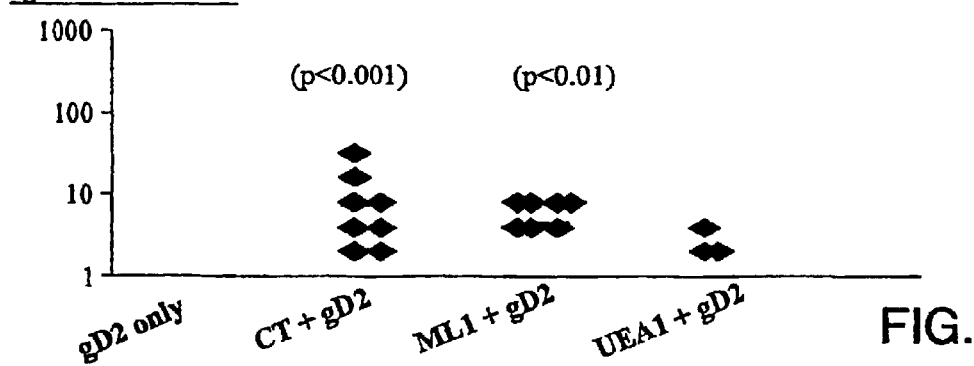
FIG. 13C, gut wash.
Figure 13D:
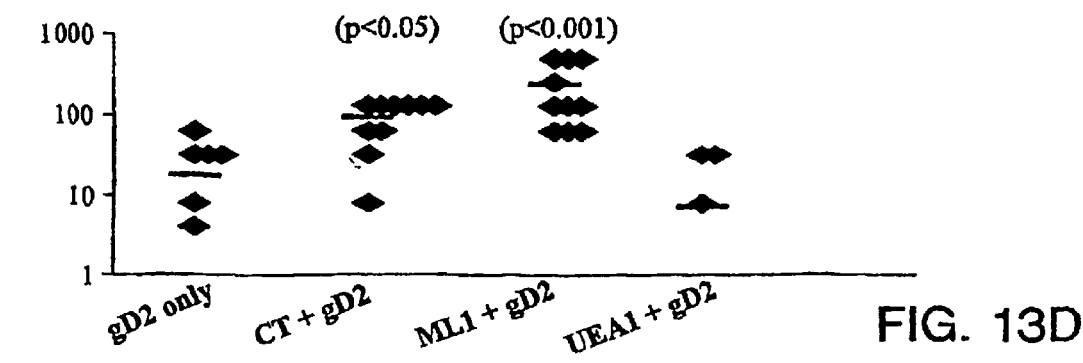
FIG. 13D, nasotracheal wash.
Figure 14A:
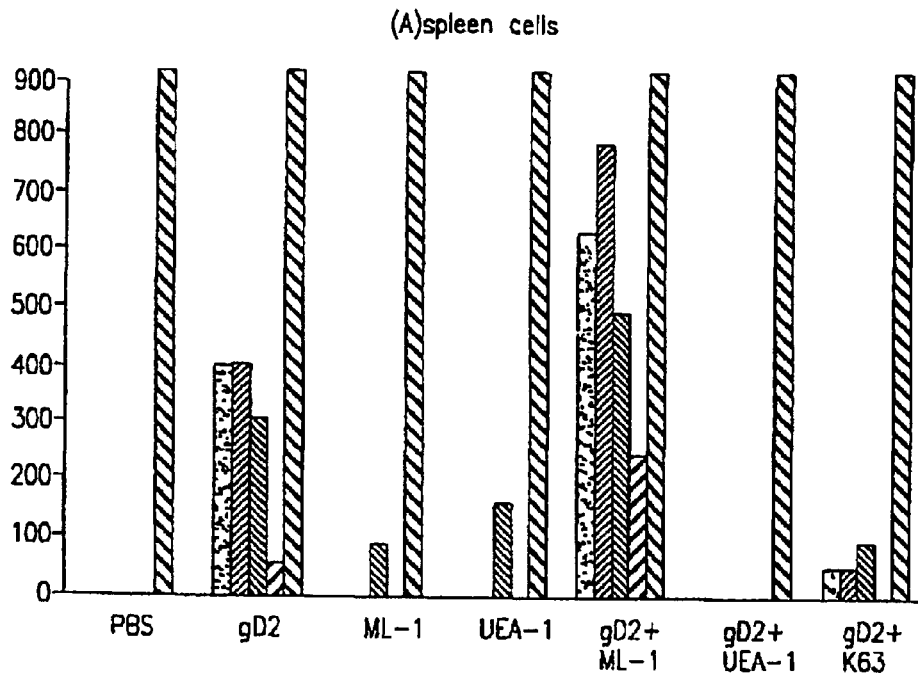
FIG. 14A, IL-5 production in spleen cells.
Figure 14B:
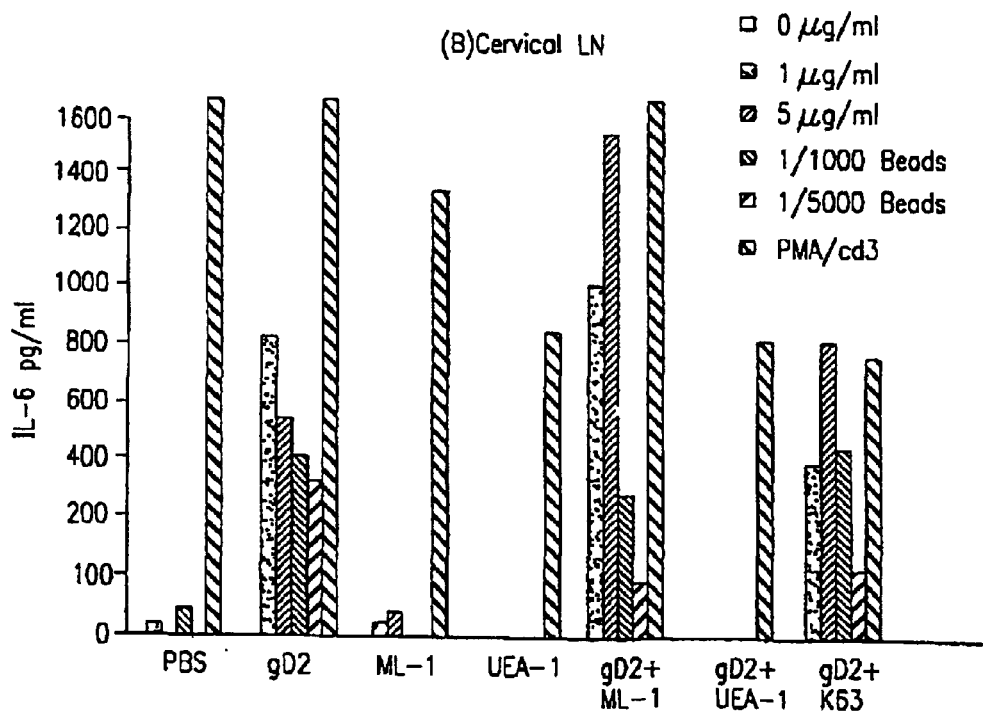
FIG. 14B, IL-5 production in cervical lymph nodes.
Figure 14C:
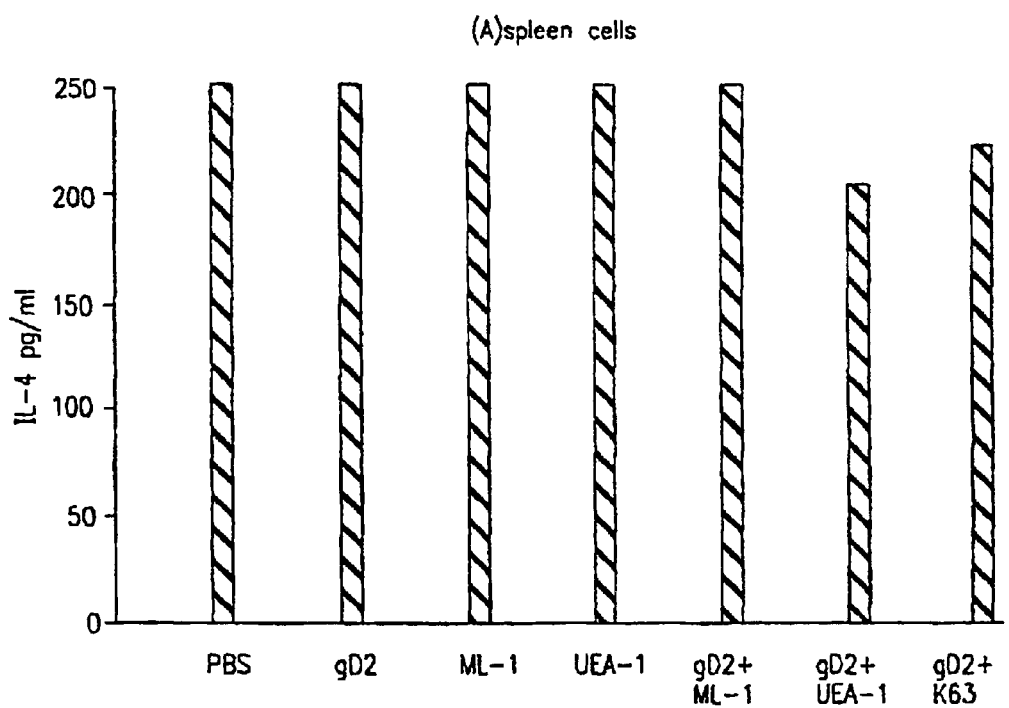
FIG. 14C, IL-4 production in spleen cells.
Figure 14D:
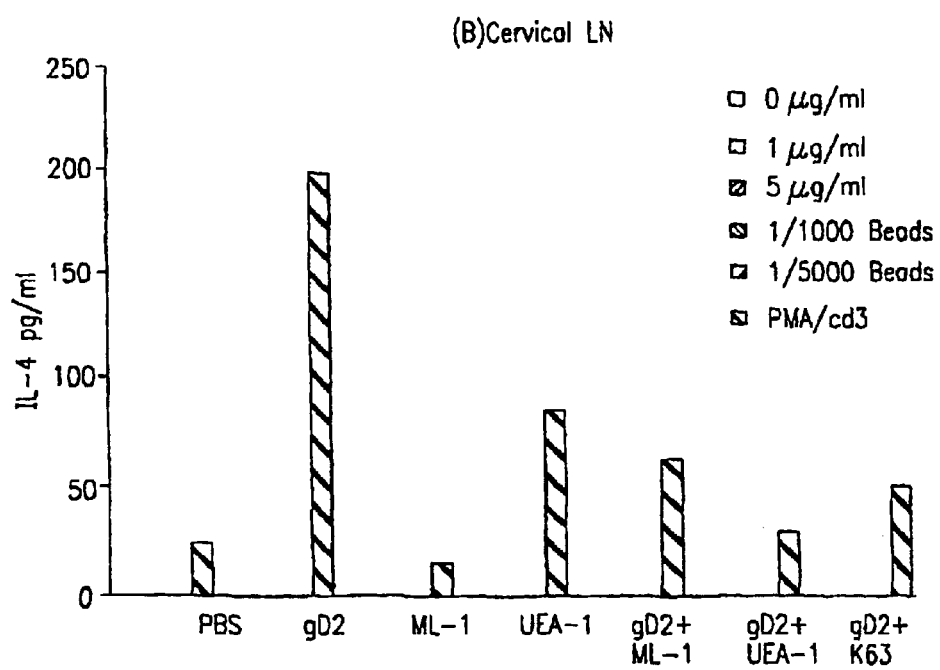
FIG. 14D, IL-4 production in cervical lymph nodes.
Figure 14E:
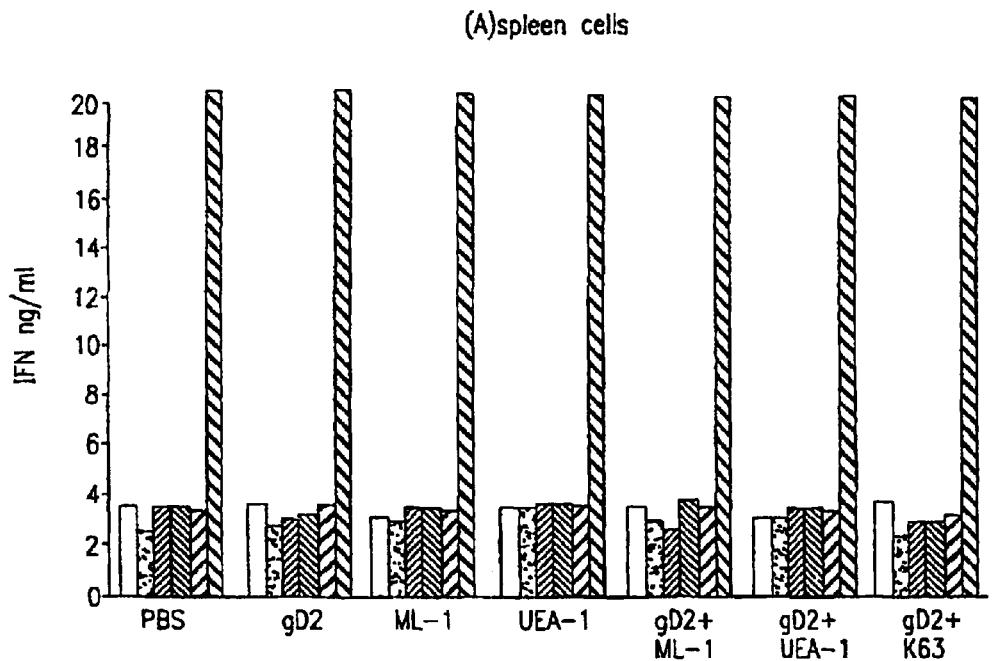
FIG. 14E, IFN production in spleen cells.
Figure 14F:
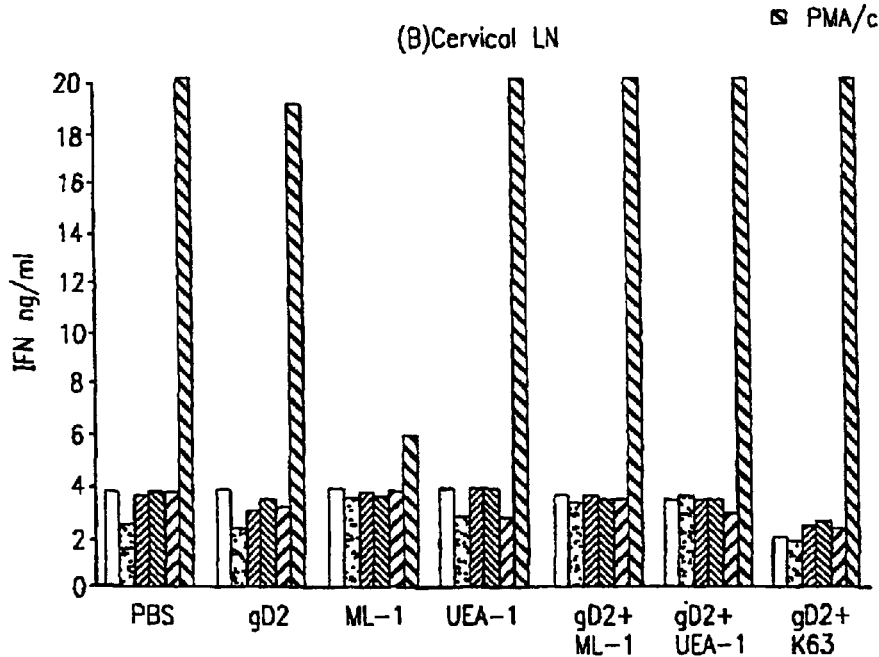
FIG. 14F, IFN production in cervical lymph nodes.
Figure 14G:
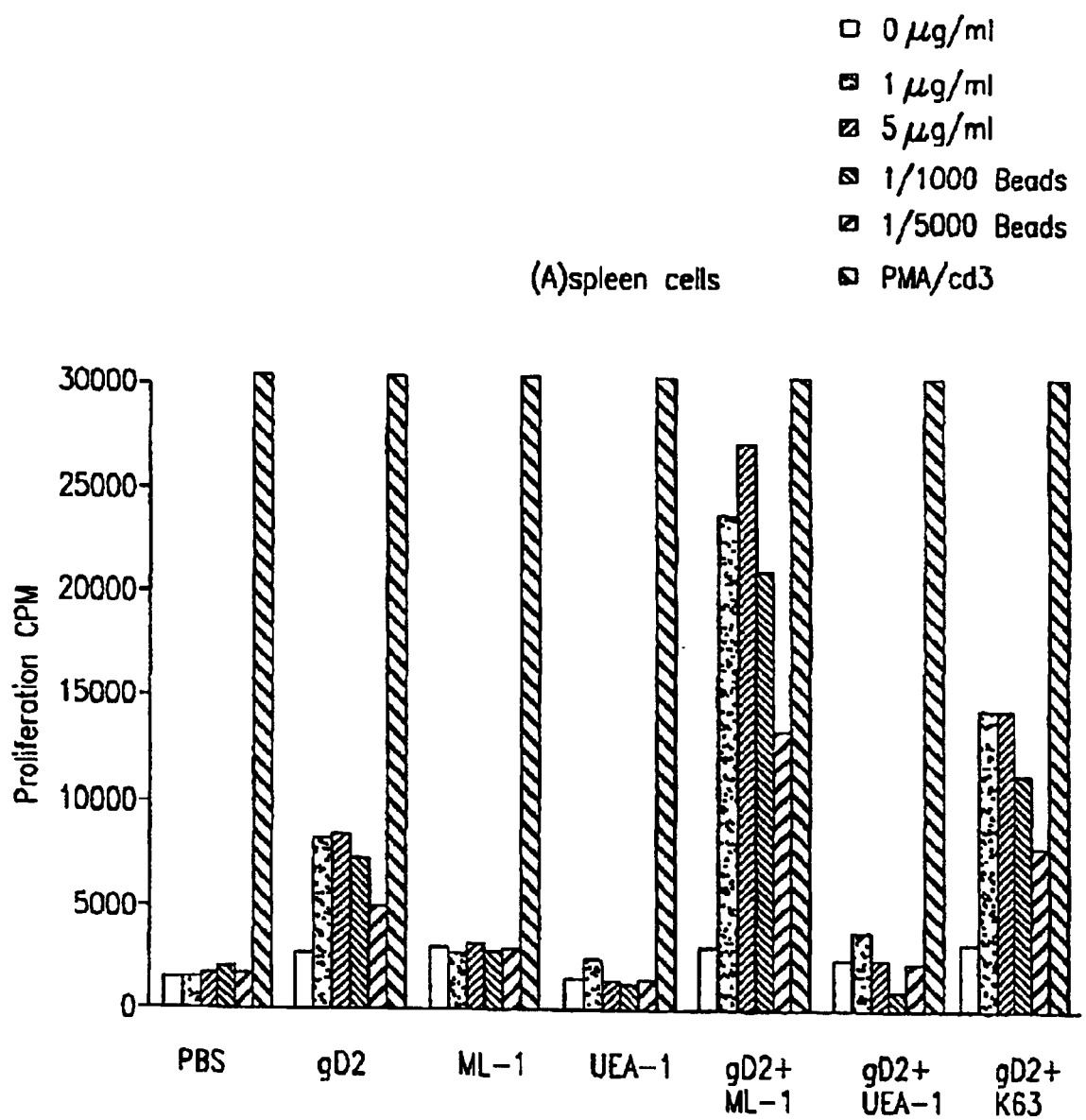
FIG. 14G, T cell proliferation by spleen cells. Responses were measured at week 8 after three immunizations (days 0, 21, 42) with gD2, MLI, or UEA-1, or with gD2+MLI, UEA-1, or LTK63. Spleen cells and cervical lymph node cells were isolated and stimulated in vitro with gD2 (0 μg/ml, 1 μg/ml, or 5 μg/ml) or with gD2 coupled to latex beads diluted 1:1000 or 1:5000 or with PMA/cd3
Figure 15A:
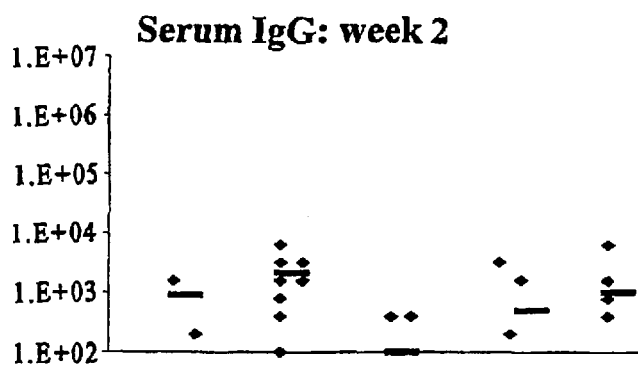
FIG. 15A, serum IgG titers after one dose (day 13.
Figure 15B:
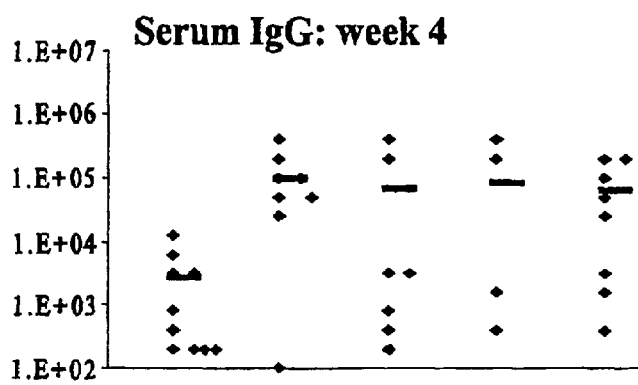
(FIG. 15B, serum IgG titers after two doses (day 27)
Figure 15C:
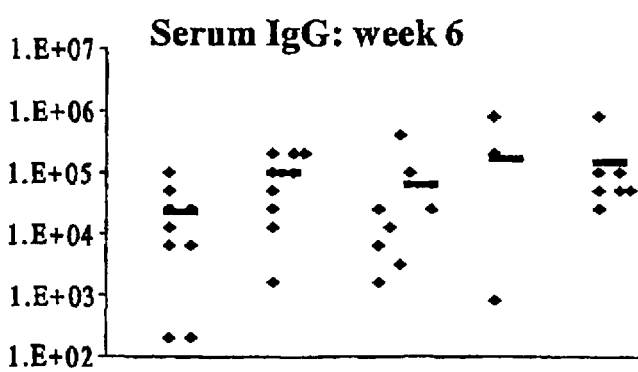
FIG. 15C, serum IgG titers after three doses (day 48.
Figure 15D:
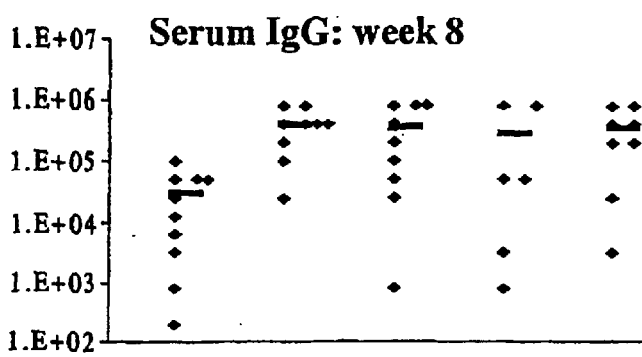
FIG. 15D, serum IgG titers after the final dose (day 62).
Figure 16A:
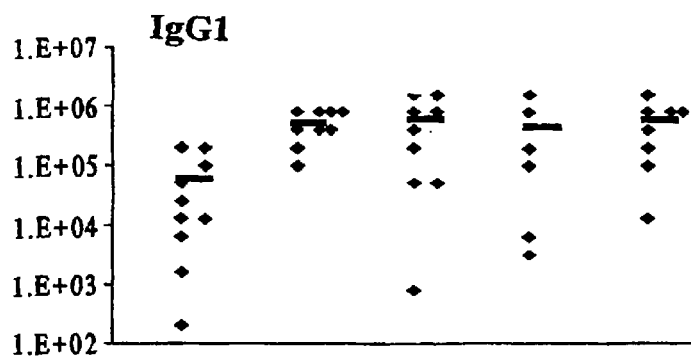
FIG. 16A, IgG1.
Figure 16B:
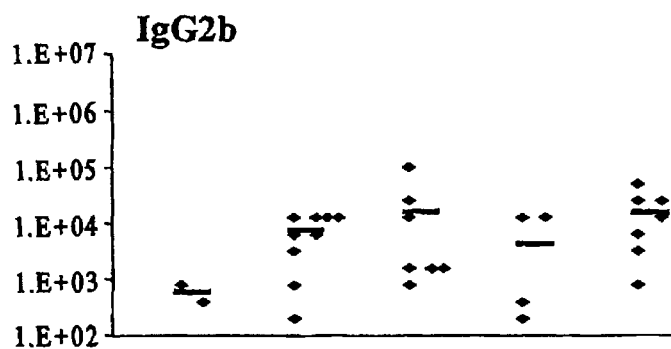
Figure 16C:
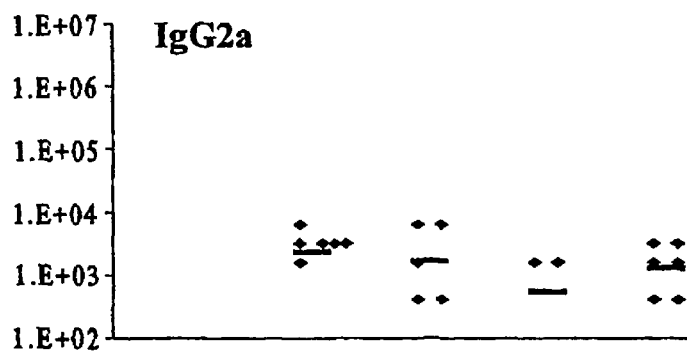
FIG. 16C. IgG2b.
Figure 16D:
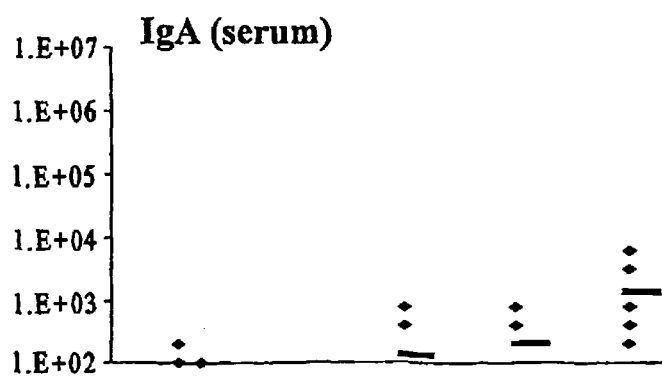
FIG. 16D, IgG3.

FIG. 12 shows gD2-specific IgG subclass antibody titers measured in mice immunized intranasally on days 1, 21, and 42 with either gD2 (5 µg) alone or gD2 (5 µg) together with 1 µg of CT, ML-I, or UEA-1. Data are titers measured in sera two weeks after the final immunization. Points refer to individual data and the symbol (−) represents the mean titer. p values in parentheses refer to significance of data compared with the gD2 only group.

FIG. 13 shows gD2-specific IgA antibody titers measured in secretions of mice immunized intranasally on days 1, 21 and 42 with either gD2 (5 µg) alone or gD2 (5 µg) together with 1 µg of CT, ML-I, or UEA-1. Data are titers measured two weeks after the final immunization in (a) saliva, (b) vaginal wash, (c) nasotracheal wash, (d) intestinal wash. Points refer to individual data and the symbol (−) represents the mean titer. p values in parentheses refer to significance of data compared with the gD2 only group.

FIG. 14 shows mean concentrations of IL-5, IL-4, and IFN production and counts per minute for T-cell proliferation assay in (a) spleen cells and (b) cervical lymph nodes at week 8 after three immunizations (days 0, 21, 42) with gD2, ML-1 or UEA-1 or with gD2 with ML-1, UEA-1 or LTK63. Spleen cells and cervical lymph node cells were isolated and stimulated in vitro with gD2 (0 µg/ml, 1 µg/ml, or 5 µg/ml) or with gD2 coupled to latex beads diluted 1:1000 or 1:5000 or with PMA/cd3.

FIG. 15 shows OVA-specific serum IgG antibody titers from mice immunized by gavage on days 1, 14, 28 and 49 with either OVA (5 mg) alone or OVA (5 mg) together with CT (10 µg), ML-I (10 µg), ML-II (10 µg) or ML-III (10 µg). Sera were collected 1 day before each immunization and at the termination of the study. FIG. 15A, serum IgG titers after one dose (day 13); FIG. 15B, serum IgG titers after two doses (day 27); FIG. 15C, serum IgG titers after three doses (day 48); FIG. 15D, serum IgG titers after the final dose (day 62). Points refer to individual data, and the symbol (−) represents the mean titer.

FIG. 16 shows OVA-specific serum IgG subclass and IgA antibody titers measured in mice immunized by gavage on days 1, 14, 35, and 49 with either OVA (5 mg) alone or OVA (5 mg) together with CT (10 µg), ML-I (10 µg), ML-II (10 µg), or ML-III (10 µg). Samples were collected two weeks after the final immunization. Data are titers measured two weeks after the final immunization. FIG. 16A, IgG1; FIG. 16B, IgG2a; FIG. 16C, IgG2b; FIG. 16D, IgG3. Points refer to individual data, and the symbol (−) represents the mean titer.

FIG. 17 shows OVA-specific IgA antibody titers measured in secretions of mice immunized by gavage on days 1, 14, 35 and 49 with OVA (5 mg) alone or OVA (5 mg)

TABLE 3

Figure 17A:
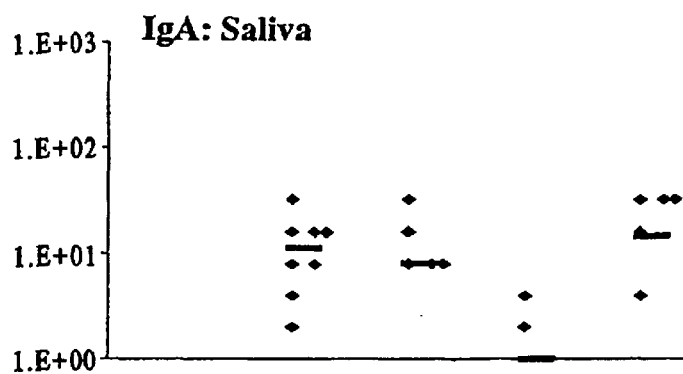
FIG. 17A, saliva, FIG. 17B, vaginal wash.
Figure 17B:
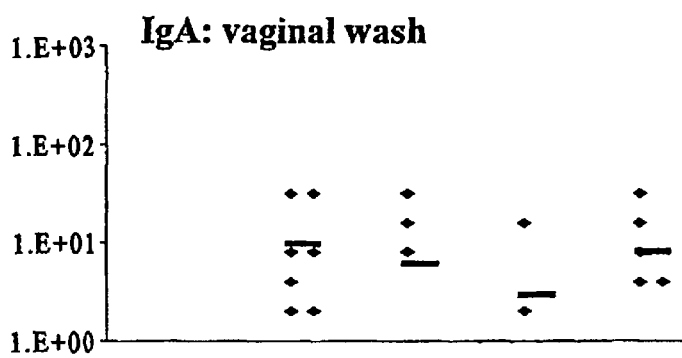
FIG. 17. OVA-specific IgA antibody titers measured in secretions of mice immunized by gavage on days 1, 14, 35 and 49 with OVA (5 mg) alone or OVA (5 mg) together with CT (10 μg), ML-I (10 μg), ML-II (10 μg), or ML-III (10 μg).
FIG. 17C, nasotracheal wash, FIG. 17D, intestinal wash.
Figure 17C:
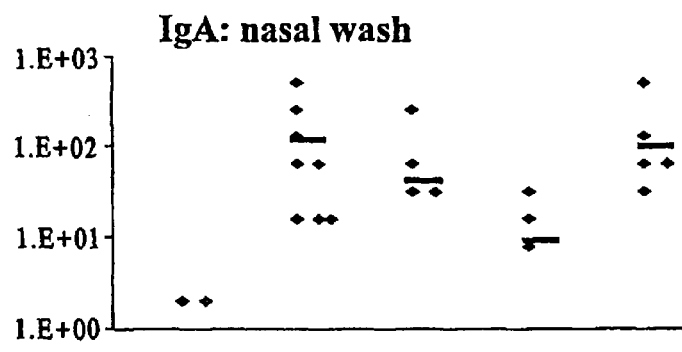
Figure 17D:
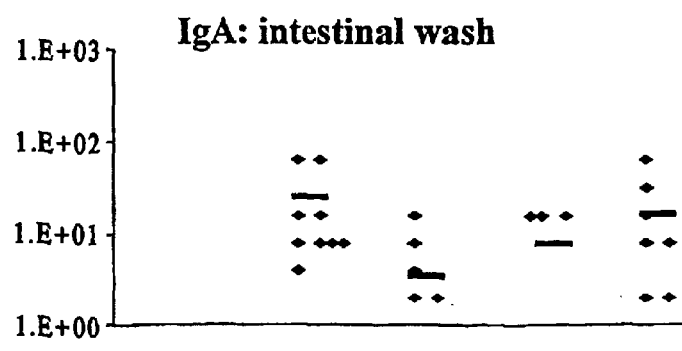

| Lectin/ toxin | Serum IgG and IgG subclass titer | | | | | IgA titer | | | | |
| --- | --- | --- | --- | --- | --- | --- | --- | --- | --- | --- |
| | IgG | IgG1 | IgG2a | IgG2b | IgG3 | Serum | Saliva | Vagina | Nasal | Gut |
| ML-I | 921600 | 1556480 | 6820 | 96000 | 10 | 1880 | 28.8 | 421 | 716.8 | 10 |
| Nigrin B | 120 | 880 | 20 | 60 | — | 10 | 0.2 | 0.4 | — | 0.6 |
| Basic Nigrin B | — | 10 | — | — | — | — | — | — | — | — |
| Ebulin r1 | 5920 | 9100 | 480 | 6160 | — | 170 | 1.6 | 0.2 | 4.4 | — |
| SNA II | 40 | 50 | — | 40 | — | 80 | — | — | 1.4 | 1 |
| SELfd | 310 | 750 | — | 90 | — | 150 | — | — | — | — | together with CT (10 μg), ML-I (10 μg), ML-II (10 μg), or ML-III (10 μg). Data are titers measured two weeks after the final immunization. FIG. 17A, saliva; FIG. 17B, vaginal wash; FIG. 17C, nasotracheal wash; FIG. 17D, intestinal wash. Points refer to individual data, and the symbol (-) represents the mean titer.

Table 4 shows OVA-specific antibody responses in mice immunized by gavage with OVA (5 mg) alone or together with lectins (10 μg) administered in 0.5 ml sodium bicarbonate. Groups of mice (n=10) were immunized on days 0, 14, 28, and 42, and samples were collected on days 56 and 57.

TABLE 4

| Lectin/toxin | Serum IgG and IgG subclass titer | | | | | IgA titer | | | | |
|---|---|---|---|---|---|---|---|---|---|---|
| | IgG | IgG1 | IgG2 | IgG2b | IgG | Serum | Saliva | Vagin | Nasal | gut |
| OVA only | 30500 | 62260 | — | 120 | — | 40 | — | — | 0.4 | — |
| ML I + OVA | 361333 | 625867 | 1689 | 16267 | — | — | 8 | 6 | 43 | 4 |
| ML II + OVA | 290800 | 462400 | 533 | 4367 | — | 133 | 1 | 3 | 9 | 8 |
| ML III + OVA | 362000 | 603200 | 1300 | 15700 | — | 200 | 15 | 8 | 100 | 17 |
| CT + OVA | 401067 | 534756 | 2311 | 7578 | — | 1375 | 11 | 10 | 119 | 26 |

Table 5 shows OVA-specific antibody responses in mice immunized with OVA (5 mg) alone or together with lectins (10 μg). Mice were administered with the antigen (±ML1) either by gavage in 0.1 ml PBS or incorporated in the feed pellet. Groups of mice (n=5) were immunized on days 0, 14, 28, and 42, and samples were collected on days 56 and 57.

Table 6 shows MLI-specific antibody responses in mice immunized orally with OVA (5 mg) alone or together with lectins (10 μg). Mice were administered with the antigen (±ML1) either by gavage in 0.1 ml PBS or incorporated in the feed pellet. Mice were immunized on days 0, 14, 28, and 42, and samples were collected on days 56 and 57.

EXAMPLE 11

Efficacy of Type II RIP (ML1, Ebulin R1) as Adjuvants when Delivered with Antigens by the Transcutaneous Route Following on from studies that demonstrated the efficacy of mistletoe lectins as mucosal adjuvants, these studies were carried out to assess the potential of type II RIP as adjuvants when administered transcutaneously. Recent work has demonstrated the effective induction of immune responses when CT is used as an adjuvant by this route (Glenn et al., 1998, 1999). In addition to ML 1, CT was used as a positive control and Ebulin r1 because it was the most immunogenic of the nontoxic type II RIP when administered intranasally.

Protocol

Groups of female Balb/c mice (n=5) were immunized on days 0 and 21 and serum samples were taken on days 0, 20, and 35 for analysis by ELISA. Three different bystander antigens, BSA, DT and gD2 were investigated. Antigens (50 μg) were administered to mice either alone or mixed with lectin/toxin (50 μg). Specific antibody responses were determined by ELISA. Additionally, the responses to CT and lectins was measured to assess their immunogenicity by the transcutaneous route. The backs of mice were shaved with a no. 40 clipper and animals were allowed to rest for 48 hr.

TABLE 5

| Lectin | Serum IgG and IgG subclass titer | | | | | IgA titer | | | | |
|---|---|---|---|---|---|---|---|---|---|---|
| | IgG | IgG1 | IgG2a | IgG2b | IgG3 | Serum | Saliva | Vagina | nasal | gut |
| OVA only | 6600 (4) | 25640 (3) | 160 (1) | 3240 (3) | — | — | — | 3.2 (1) | — | — |
| ML I + OVA (PBS) (PBS) | 6120 (5) | 8340 (5) | — | — | — | 80 (1) | — | — | — | 2 (2) |
| OVA ONLY (PELLET) | 20 (1) | 40 (1) | — | — | — | — | — | — | — | — |
| ML I + OVA (PELLET) | 160 (3) | 20 (1) | — | 40 (2) | — | — | — | — | — | 0.4 (1) |

TABLE 6

| Lectin | Serum IgG and IgG subclass titer | | | | | IgA titer | | | | |
|---|---|---|---|---|---|---|---|---|---|---|
| | IgG | IgG1 | IgG2a | IgG2b | IgG3 | Serum | Saliva | Vagina | Nasal | Gut |
| OVA ONLY (PBS) | | | | | | | | | | |
| ML I + OVA (PBS) | 6080 (5) | 33280 (5) | 240 (2) | 4640 (5) | — | 1440 (5) | 0.4 (1) | 2 (3) | 0.4 (1) | 16 (5) |
| OVA ONLY PELLET) | | | | | | | | | | |
| ML I + OVA (PELLET) | 6600 (5) | 31040 (5) | 120 (2) | 2260 (5) | — | 560 (4) | — | 35.2 (4) | 0.8 (1) | 3.2 (3) |

Mice were anesthetized with hypnorm-diazepam during the immunization procedure. The skin was swabbed with ethanol 1 min prior to application of solution. Immunizing solution (100 μl) was applied to shaved skin over a 2 cm² area. After 30 min, a further 100 μl of distilled water was applied and mice were left for 90 min. Mice were extensively washed with lukewarm tap water, patted dry, and washed again.

Study Groups

I. BSA
1. BSA 50 µg
2. BSA 50 µg+CT 50 µg
3. BSA 50 µg+ML I 50 µg
4. BSA 50 µg+Ebulin r1 50 µg II. Diphtheria Toxoid (DT)
1. DT 50 µg
2. DT 50 µg+CT50 µg
3. DT 50 µg+ML I 50 µg
4. DT 50 µg+Ebulin r1 50 µg III. Herpes Simplex Virus 2 Glycoprotein D (gD2)
1. gD2 50 µg
2. gD2 50 µg+CT 50 µg
3. gD2 50 µg+ML 1 50 µg
4. gD2 50 µg+lectin II 50 µg Table 7 shows BSA-specific serum antibody titers measured following 1 and 2 transcutaneous doses of BSA (50 µg) alone or together with CT/plant lectin (50 µg).

TABLE 7

| Adjuvant/antigen | Mouse number | Serum IgG titer week 3 | Serum IgG titer week 5 | Serum IgG1 titer week 5 | Serum IgG2a titer week 5 |
|---|---|---|---|---|---|
| BSA | 1 | 100 | 100 | 100 | <100 |
|  | 2 | <100 | 6400 | 6400 | <100 |
|  | 3 | <100 | 25600 | 25600 | <100 |
|  | 4 | <100 | 1600 | 1600 | <100 |
|  | 5 | <100 | 12800 | 12800 | <100 |
| CT + BSA | 1 | <100 | 819200 | 819200 | <100 |
|  | 2 | 3200 | 1638400 | 1638400 | 12800 |
|  | 3 | 6400 | 409600 | 409600 | 1600 |
|  | 4 | 1600 | 819200 | 819200 | 3200 |
|  | 5 | 400 | 819200 | 819200 | 800 |
| ML1 + BSA | 1 | 800 | 102400 | 102400 | <100 |
|  | 2 | 1600 | 204800 | 204800 | 1600 |
|  | 3 | 1600 | 204800 | 204800 | 400 |
|  | 4 | <100 | 409600 | 409600 | <100 |
|  | 5 | <100 | 204800 | 204800 | 200 |
| Ebulin r1 + BSA | 1 | <100 | 102400 | 102400 | <100 |
|  | 2 | 800 | 204800 | 25600 | <100 |
|  | 3 | 200 | 204800 | 102400 | <100 |
|  | 4 | <100 | 409600 | 204800 | <100 |
|  | 5 | <100 | 204800 | 204800 | <100 |

Table 8 shows DT-specific serum antibody titers measured following 1 and 2 transcutaneous doses of DT (50 µg) alone or together with CT/plant lectin (50 µg).

TABLE 8

| Adjuvant/antigen | Mouse number | Serum IgG titer week 3 | Serum IgG titer week 5 | Serum IgG1 titer week 5 | Serum IgG titer week 5 |
|---|---|---|---|---|---|
| DT | 1 | 100 | <100 | 200 | <100 |
|  | 2 | <100 | 25600 | 102400 | <100 |
|  | 3 | <100 | 12800 | 25600 | 100 |
|  | 4 | 100 | 800 | 3200 | <100 |
|  | 5 | <100 | 100 | 100 | <100 |
| CT + DT | 1 | 25600 | 1638400 | 1638400 | 800 |
|  | 2 | 12800 | 1638400 | 1638400 | 1600 |
|  | 3 | 25600 | 3276800 | 6553600 | 3200 |
|  | 4 | 25600 | 1638400 | 3276800 | 3200 |
|  | 5 | 51200 | 819200 | 1638400 | 1600 |

TABLE 8-continued

| Adjuvant/antigen | Mouse number | Serum IgG titer week 3 | Serum IgG titer week 5 | Serum IgG1 titer week 5 | Serum IgG titer week 5 |
|---|---|---|---|---|---|
| ML1 + DT | 1 | 800 | 51200 | 102400 | <100 |
|  | 2 | 100 | 25600 | 102400 | 100 |
|  | 3 | <100 | 6400 | 12800 | <100 |
|  | 4 | <100 | 51200 | 102400 | 100 |
|  | 5 | <100 | 6400 | 12800 | 100 |
| Ebulin r1 + DT | 1 | <100 | 400 | 800 | <100 |
|  | 2 | 800 | 100 | 200 | <100 |
|  | 3 | 1600 | 102400 | 204800 | 100 |
|  | 4 | 400 | 12800 | 25600 | <100 |
|  | 5 | <100 | 51200 | 204800 | <100 |

Table 9 shows gD2-specific serum antibody titers measured following 1 and 2 transcutaneous doses of gD2 (50 µg) alone or together with CT/plant lectin (50 µg). Due to the poor responses, serum IgGa and IgG1 levels were not determined.

TABLE 9

| Adjuvant/antigen | Mouse number | Serum IgG titer week 3 | Serum IgG titer week 5 |
|---|---|---|---|
| gD2 | 1 | <100 | <100 |
|  | 2 | 100 | 100 |
|  | 3 | <100 | <100 |
|  | 4 | <100 | <100 |
|  | 5 | <100 | <100 |
| CT + gD2 | 1 | 100 | 1600 |
|  | 2 | <100 | 102400 |
|  | 3 | <100 | 3200 |
|  | 4 | <100 | 3200 |
|  | 5 | <100 | 6400 |
| ML1 + gD2 | 1 | <100 | <100 |
|  | 2 | <100 | <100 |
|  | 3 | <100 | 1600 |
|  | 4 | <100 | <100 |
|  | 5 | <100 | <100 |
| Ebulin r1 + gD2 | 1 | <100 | <100 |
|  | 2 | <100 | <100 |
|  | 3 | 100 | <100 |
|  | 4 | 100 | 200 |
|  | 5 | 100 | <100 |

Table 10 shows CT and lectin-specific serum antibody titers measured following 1 and 2 transcutaneous doses with CT/ML1/Ebulin r1 (50 µg).

TABLE 10

| Lectin/toxin | Mouse number | Serum IgG titer week 3 | Serum IgG titer week 5 |
|---|---|---|---|
| CT | 1 | 3200 | 102400 |
|  | 2 | 3200 | 51200 |
|  | 3 | 3200 | 12800 |
|  | 4 | <100 | 204800 |
|  | 5 | 204800 | 1638400 |
|  | 6 | 12800 | 102400 |
|  | 7 | 12800 | 204800 |
|  | 8 | 3200 | 204800 |
|  | 9 | 3200 | 102400 |
|  | 10 | 800 | 204800 |
|  | 11 | <100 | 102400 |
|  | 12 | <100 | 819200 |
|  | 13 | <100 | 102400 |
|  | 14 | 800 | 409600 |
|  | 15 | 800 | 102400 |

TABLE 10-continued

| Lectin/toxin | Mouse number | Serum IgG titer week 3 | Serum IgG titer week 5 |
|---|---|---|---|
| ML1 | 1 | 800 | 1600 |
| | 2 | 400 | 3200 |
| | 3 | 400 | 1600 |
| | 4 | 800 | 51200 |
| | 5 | <100 | 25600 |
| | 6 | <100 | <100 |
| | 7 | <100 | 400 |
| | 8 | <100 | <100 |
| | 9 | <100 | 800 |
| | 10 | <100 | <100 |
| | 11 | <100 | 12800 |
| | 12 | <100 | 1600 |
| | 13 | <100 | 1600 |
| | 14 | <100 | 25600 |
| | 15 | <100 | 200 |
| Ebulin r1 | 1 | <100 | 400 |
| | 2 | 100 | <100 |
| | 3 | 100 | <100 |
| | 4 | 800 | 200 |
| | 5 | 200 | <100 |
| | 6 | 100 | <100 |
| | 7 | 100 | <100 |
| | 8 | <100 | 100 |
| | 9 | <100 | <100 |
| | 10 | <100 | <100 |
| | 11 | <100 | <100 |
| | 12 | <100 | <100 |
| | 13 | <100 | 100 |
| | 14 | <100 | 400 |
| | 15 | 100 | <100 |

EXAMPLE 12

Binding, Uptake and Translocation of Orally Delivered Lectins in Mice

Administration of lectins and collection of tissues. Female Balb/c mice were maintained on a normal stock diet with free access to water prior to experiments. Mice were deprived of food overnight and lectins were delivered by gavage using curved oral dosing needles (20 g×25 mm) (1 mg lectin/mouse in 100 μl physiological saline) to groups of 24 mice. Water was available throughout. Groups of 8 animals were sacrificed by halothane anesthesia followed by exsanguination after 1 hr, 6 hr and 24 hr. Blood was collected by cardiac puncture. Mice were dissected, and the entire gut was removed and divided into stomach, two parts of small intestine and large intestine. Gut contents were washed out with 10 ml of ice-cold PBS to give an indication of the amount of unbound lectin present. Gut tissues were placed in polythene bags and snap frozen in liquid nitrogen. Sections of intestine were taken in each case and fixed in 4% formalin for examination of lectin binding by histology. All gut tissues and washings were stored at −20° C. until required for analysis. Additionally, the liver, spleen and kidneys were collected from animals.

Extraction of lectins from tissue. Tissues from animals administered with lectins or with control saline were extracted by homogenization in a 20 mM solution of diaminopropane. Tissue pieces were placed in the extracting solution (995 μl 20 mM diaminopropane+5 μl of 5 mg ml$^{-1}$ Aprotinin (Sigma)) and homogenized (Janke and Kunkel IKA®-Labortechnik, Ultra-Turrax®) at 24000 rpm for 2 minutes on ice. The homogeniser head was washed with distilled water, in 1 ml of extracting solution and again in distilled water between samples. Samples was centrifuged (Jouan, MRI 22) for 20 min at 18600 g at 2° C. The supernatants were collected and stored at −20° C. until required for analysis.

Processing of gut washing. To provide an indication of the amount of free (unbound) lectin present in the gut, the amount of lectin present in gut washings was analysed. Washings (500 μl) were added to dilution buffer (495 μl)+the protease inhibitor Aprotinin (5 μl of 5 mg ml$^{-1}$) and centrifuged (Microspin 12S, Sorvall® Instruments, Du Pont) at 8000 rpm for 10 min.

Processing of blood samples. After collection, blood samples were left at room temperature for 1 hour and centrifuged at 7000 rpm for 6 min (Microspin 12S, Sorvall® Instruments, Du Pont). Plasma was collected and stored at −20° C. until required for analysis.

ELISA analysis of binding of plant lectins to the gut. An ELISA assay was set up to enable the quantification of WGA in extracted tissue samples and washings. Microtiter plates (Immunolon 4, Dynatech) were coated with 75 μl a 1:64000 dilution of rabbit anti-WGA per well in carbonate-bicarbonate buffer, pH 9.6 and incubated at 4° C. overnight. After washing, plates were blocked with PBST/2% gelatin/200 mM N-acetylglucosamine and incubated at 37° C. for 1 hr. Plates were washed; standards and samples added, serially diluted in dilution buffer (PBST/200 mM N-acetylglucosamine) and incubated at 37° C. for 1 hr. A standard curve for WGA was constructed by titrating a WGA solution from 10 ng/ml to 78 pg/ml. Biotinylated anti-WGA at a dilution of 1:16000 in dilution buffer was added and incubated at 37° C. for 1 hr. After further washes, ExtrAvidin® peroxidase (Sigma) at a dilution of 1:1000, in dilution buffer was added and incubated at 37° C. for 30 min. Plates were washed and 50 μl/well of developing solution (TMB microwell peroxidase substrate (1-C) Kirkegaard and Perry Laboratories, Gaithersburg, USA) was added and incubated in the dark with shaking at 37° C. for 30 min. The reaction was stopped by addition of 1 M H2SO4 (50 μl/well) and the absorbance read at 450 nm. WGA levels were calculated from the linear region of the standard curve.

SDS-PAGE and Western Blotting. SDS-PAGE gels were run and proteins transferred to PVDF membranes using a semi-dry transfer apparatus. After transfer, membranes were blocked in a 2.5% casein solution for 30 min at room temperature. Membranes were washed and the primary antibody (biotin-labeled anti-lectin) was added at a dilution of 1:2500 in 5 ml of 1.2% casein solution. Following incubation with agitation at room temperature overnight, membranes were washed extensively with PBS and ExtrAvidin® peroxidase added at a 1:5000 dilution in 1.2% casein. Following a 1 hr incubation at room temperature, membranes were washed extensively with PBS and distilled water. Excess fluid was blotted from membranes and the developing solution was added (Super signal® West pico detection kit (Pierce, Rockford, USA)) and left in the dark for 5 min. Excess fluid was dried from membranes and membranes were exposed to film (Kodak X-OMAT LS (Sigma)) and processed.

Results

Figure 18:
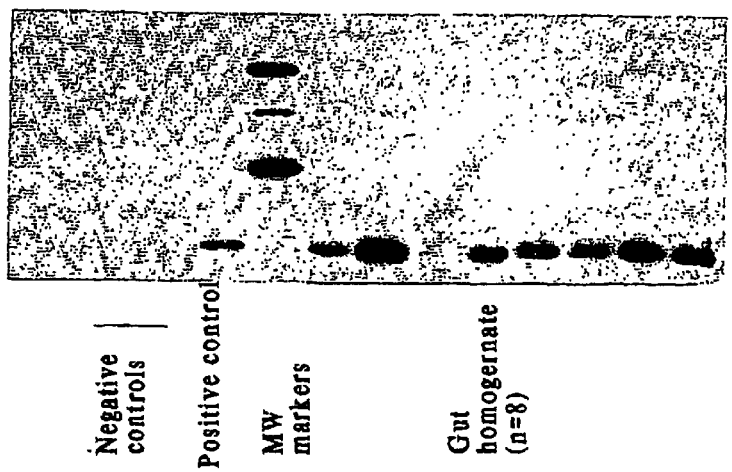
FIG. 18. Western blot showing WGA in gut homogenates collected from mice 6 hours following gavage with a single dose of 1 mg WGA.
Figure 19:
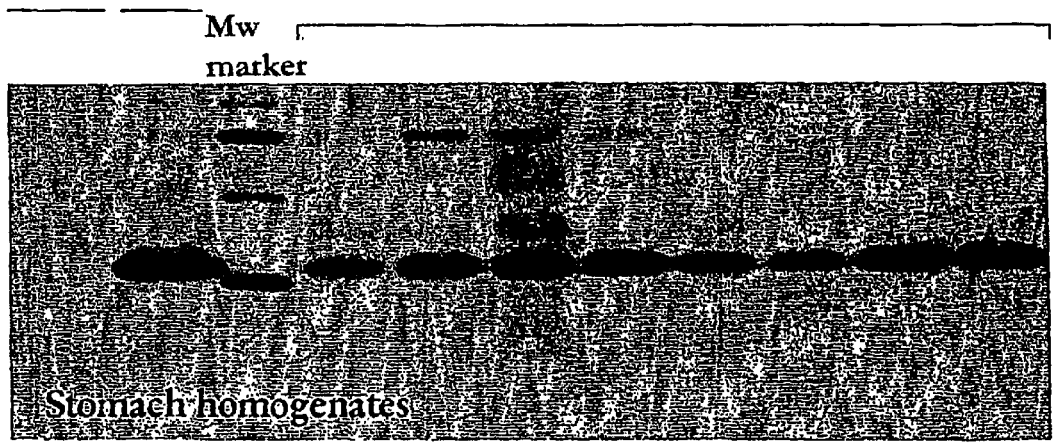
FIG. 19. Western blots showing homogenized stomach tissues and small intestine washings collected 1 hour after gavage with a single dose of 1 mg PHA.
Figure 19:
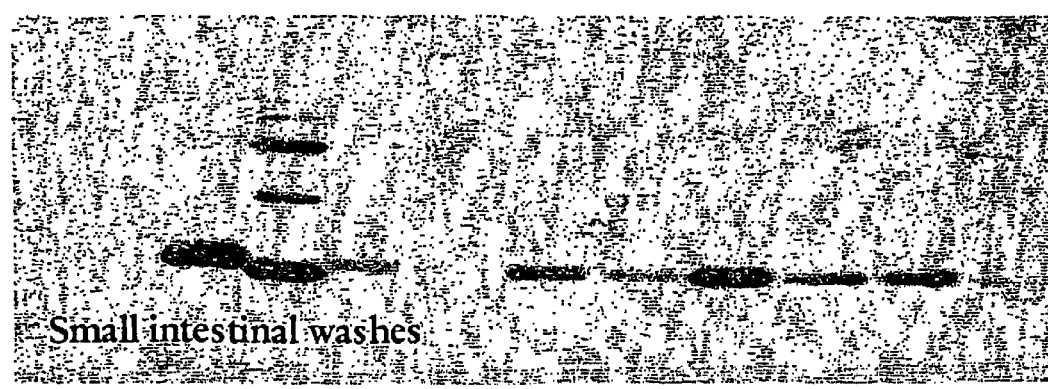

Stability and binding of plant lectins in the mouse gut following oral gavage. The lectins, PHA, WGA and UEA-1 were stable in the mouse digestive tract for up to 6 hr after gavage (Tables 11 and 12; FIGS. 18 and 19). In the small intestine, the lectins were only detected at the subunit MW of the positive control. In the stomach there was an indication of lectin aggregation after 6 and 24 hr in the cases of PHA and UEA-1. However, most of the lectin detected in the stomach was also intact. Analysis of lectin binding to the gut found differences in the location of lectin binding at 1 and 6 hr after delivery. PHA (and WGA, not presented) bound to the proximal small intestine while UEA-1 was not detected in this region but bound to the distal small intestine (Table 11). The pattern of binding was similar at 1 and 6 hr after lectin administration. At 24 hr after delivery, lectins were not detected in homogenised gut tissues. This indicated that lectins did not detach from the gut and re-bind but more likely were excreted after detachment.

Table 11 shows detection of PHA (isotype E2L2) in the mouse digestive tract at 1, 6, and 24 hr after the delivery of 1 mg by gavage. The + symbol indicates that lectin was detected on Western blots and the number of mice with a positive signal (out of 8 in each case) is presented in parentheses. The positive control PHA subunit molecular weight was 29.5 kDa.

Table 12 shows detection of UEA1 in the mouse digestive tract at 1, 6, and 24 hr after the delivery of 1 mg by gavage. The + symbol indicates that lectin was detected on Western blots and the number of mice with a positive signal (out of 8 in each case) is presented in parentheses. The positive control UEA1 apparent subunit molecular weight was 34.7 kDa.

TABLE 11

| GUT REGION | TIME AFTER DELIVERY (hr) | MW (kDa) | | | | | | | |
|---|---|---|---|---|---|---|---|---|---|
| | | 125.9 | 114.8 | 91.2 | 58.1 | 43.7 | 29.5 | 9.3 | 7.6 |
| Gut wash | 1 | — | — | — | — | — | + (8) | — | — |
| | 6 | — | — | — | — | — | — | — | — |
| | 24 | — | — | — | — | — | — | — | — |
| Stomach | 1 | — | — | — | + (7) | — | + (8) | — | — |
| | 6 | — | — | — | + (3) | — | — | — | — |
| | 24 | — | — | — | — | — | — | + (4) | + (4) |
| Small intestine Homogenate (Proximal) | 1 | — | — | — | — | — | + (8) | — | — |
| | 6 | — | — | — | — | — | + (8) | — | — |
| | 24 | — | — | — | — | — | — | — | — |
| Small intestine Homogenate (Distal) | 1 | | | | | | | | |
| | 6 | — | — | — | — | — | + (6) | — | — |
| | 24 | — | — | — | — | — | — | — | — |
| Large intestine Homogenate | 1 | — | — | — | — | — | — | — | — |
| | 6 | — | — | — | — | — | — | — | — |
| | 24 | — | — | — | — | — | — | — | — |

TABLE 12

| GUT REGION | TIME AFTER DELIVERY (hr) | APPARENT MOLECULAR WEIGHT (kDa) | | | | | | | |
|---|---|---|---|---|---|---|---|---|---|
| | | 144.5 | 114.8 | 100 | 87.1 | 75.9 | 64.6 | 52.5 | 34.7 |
| Stomach | 1 | — | — | — | — | — | — | — | + (4) |
| | 6 | — | — | — | + (4) | + (3) | + (3) | — | — |
| | 24 | — | — | — | + (1) | — | + (3) | — | — |
| Small intestine Wash | 1 | — | — | + (2) | — | + (1) | — | — | + (4) |
| | 6 | — | — | — | — | — | — | — | — |
| | 24 | — | — | — | — | — | — | — | — |
| Small intestine homogenate (Proximal) | 1 | — | — | — | — | — | — | — | — |
| | 6 | — | — | — | — | — | — | — | — |
| | 24 | — | — | — | — | — | — | — | — |
| Small intestine homogenate (Distal) | 1 | — | — | — | — | — | — | — | + (4) |
| | 6 | — | — | — | — | — | — | — | + (5) |
| | 24 | — | — | — | — | — | — | — | — |
| Large intestine homogenate | 1 | — | — | — | — | — | — | — | + (2) |
| | 6 | — | — | — | — | — | — | — | + (4) |
| | 24 | — | — | — | — | — | — | — | — |

Figure 20:
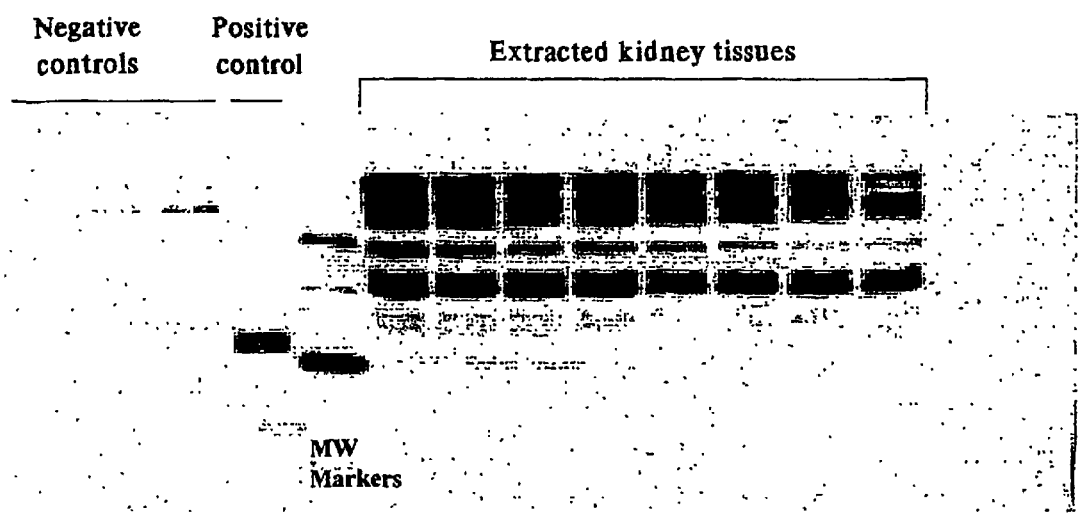
FIG. 20. Western blot showing UEA1 in extracted mouse kidney tissues collected 24 hours following gavage with a single dose of 1 mg of UEA1.
Figure 21:
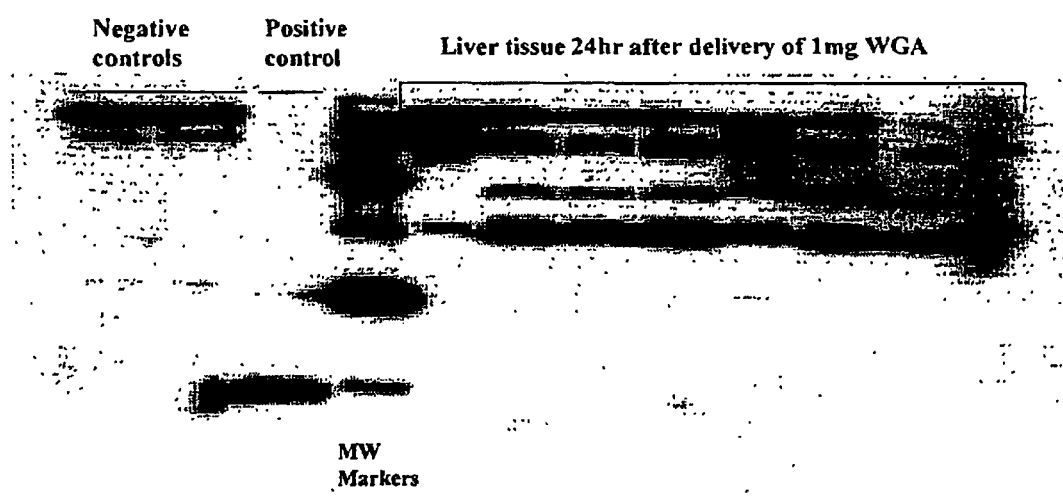
FIG. 21. Western blot showing WGA in mouse liver tissues collected 24 hours following gavage with a single dose of 1 mg WGA.

Detection of lectins in internal organs and blood. Sensitive chemiluminescent Western blotting assays were used to determine lectin uptake. For all three lectins, uptake into the liver and kidney was measured (Table 13, FIGS. 20 and 21). FIG. 20 shows that UEA1 detected in kidney tissue are at a higher molecular weight than in the positive control. There is a cross reaction with control kidney tissue. However, additional bands are visible in mouse tissues from animals administered with lectin. These bands are at a higher molecular weight than in the control.

Lectins were detected in liver tissue from 1 to 24 hr after administration. However, the MW of the reactive bands was considerably higher than the expected subunit MW. In fact, none of the 3 lectins were detected at the expected subunit WM in internal organs. To get an indication of the degree of lectin uptake, a sandwich ELISA was set up to quantify WGA. This enabled a determination of lectins in the gut and internal organs (Table 13). The lectin was detected in gut homogenates for up to 6 hr after delivery at approximately the level of lectin administered. At 24 hr, no lectin was detected in homogenates. Of the internal organs, the highest levels of lectin were detected in liver tissue. The level of lectin at this site increased from 1 to 24 hr. However, the highest amount of lectin detected (289.3 ng) represented a small fraction of the delivered dose. Very low levels of WGA were detected in the blood cells or sera or in the spleen. The detection of the highest level of lectin in the liver and kidney is in line with the Western blotting results where the lectins were detectable in the liver and kidney tissue but not in blood or the other organs.

Figure 22:
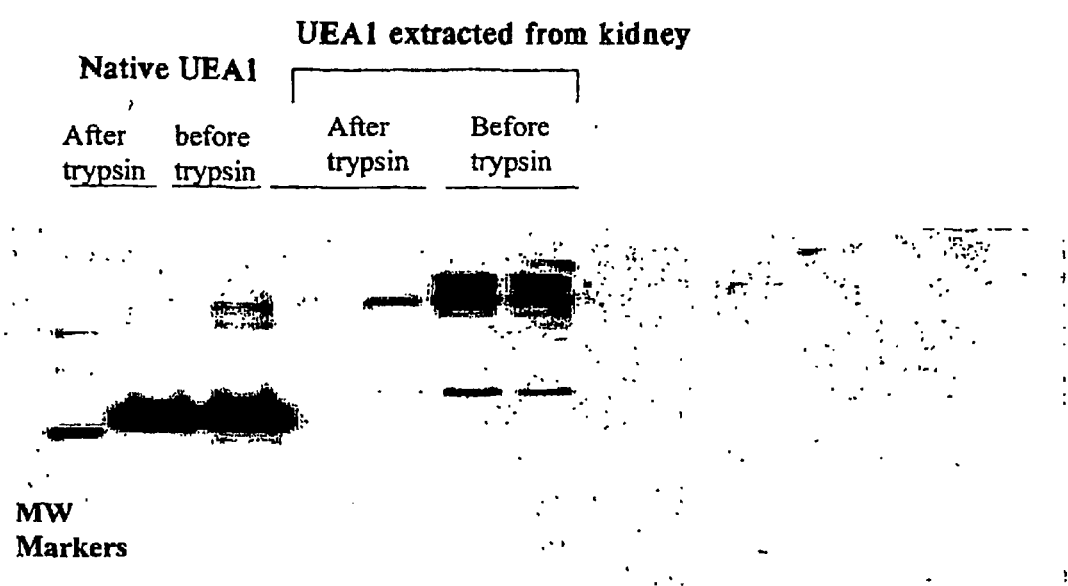
FIG. 22. Western blot showing the susceptibility of native and kidney-extracted UEA1 to digestion by trypsin.

Stability of native and absorbed lectins to proteolysis by trypsin. To determine if the absorbed lectins detected in the liver and kidneys retained the properties of the native lectins, native and tissue-extracted PHA, WGA and UEA-1 were incubated for 1 hr with a solution of trypsin. All three lectins were highly stable to the enzyme in their native form. However, the modified lectins detected in liver and kidney tissue were degraded by the enzyme (FIG. 22). This indicates that cells in the liver and kidney are capable of modifying plant lectins to forms which are sensitive to proteolysis. This may be a mechanism for degradation of ingested plant lectins which survive in the digestive tract and are absorbed.

TABLE 13 shows detection of WGA in tissues following oral gavage of groups of mice (n=8) with a single dose of 1 mg lectin in 0.1 ml PBS. The lectin was determined by a quantitative sandwich ELISA and the data are presented as $\mu$g lectin per organ or per ml for blood.

TABLE 13

| TISSUE | TIME AFTER LECTIN DELIVERY (hr) | | |
|---|---|---|---|
| | 1 | 6 | 24 |
| Gut homogenate | ND | 1018.1 ± 949.2 | — |
| Gut wash | 5.5 ± 5.8 | 2.5 ± 1.4 | 0.4 ± 0.7 |
| Liver | 28.5 ± 33 | 48 ± 42.1 | 289.3 ± 546 |
| Spleen | 0.6 ± 0.9 | 3.3 ± 2.1 | 11.9 ± 9.2 |
| Kidney | 0.5 ± 0.5 | 1.9 ± 0.8 | 1.6 ± 2.2 |
| Serum | 0.4 ± 0.7 | 2.1 ± 1.8 | 1.1 ± 2 |
| Blood cells | 0.3 ± 0.5 | 1.8 ± 2.5 | 0.5 ± 0.8 |

References

1. McGhee, J. R. and Kiyono, H. 1999. The mucosal immune system, p. 909–945. In W. E. Paul (ed.), Fundamental Immunology, 4th ed. Lippincott-Raven Publishers, Philadelphia.
2. Robertson, S. M., and Cebra, J. J. 1976. A model for local immunity. Ric Clin Lab. 6: 105.
3. Winner, L. III, Mack, J., Weltzin, R., Mekalanos, J. J., Krachenbuhl, J. P., and Neutra, M. R. 1991. New model for analysis of mucosal immunity: intestinal secretion of specific monoclonal immunoglobulin A from hybridoma tumors protects against Vibrio cholerae infection. Infect Immun 59: 977–982.
4. Nossal G. J. V. 1999. Vaccines, p. 1387–1425. In: W. E. Paul (ed.), Fundamental Immunogy, 4th ed. Lippinncott-Raven Publishers, Philadelphia.
5. Ward, S. J., Douce, G., Figueiredo, D., Dougan, G., and Wren, B. W. 1991. Immunogenicity of a Salmonella typhimurium aroA aroD vaccine expressing a nontoxic domain of Clostridium difficile toxin A. Infect Immun. 67:2145–2152.
6. O'Hagan, D. T. 1998. Microparticles and polymers for the mucosal delivery of vaccines. Adv. Drug. Deliv. Rev. 34: 305–320.
7. Rogers, J. A., and Anderson, K. E. 1998. The potential of liposomes in oral drug delivery. Crit. Rev. Ther. Drug. Carrier. Syst. 15: 421–480.
8. Elson C. J., and Ealding W. 1984. Generalised systemic and mucosal immunity in mice after mucosal stimulation with cholera toxin. J. Immunol. 132: 2736–2741.
9. Clements, J. D., Hartzog N. M. and Lyon F. L. 1988. Adjuvant activity of Escherichia coli heat-labile enterotoxin and effect on the induction of oral tolerance in mice to unrelated protein antigens. Vaccine, 6: 269–277.
10. Lycke, N. 1997. The mechanism of cholera toxin adjuvanticity. Res. Immunol. 148: 504–520.
11. Williams N. A., Hirst T. R., and Nashar T. O. 1999. Immune modulation by the choleralike enterotoxins: from adjuvant to therapeutic. Immunol. Today. 20: 95–101.
12. Pizza M., Domenighini M., Hol W., Giannelli V., Fontana M. R., Guiliani M., Magagnoli C., Peppoloni S., Manetti R., and Rappuoli R. 1994. Probing the structure activity relationship of Escherichia coli LT-A by site-directed mutagensis. Mol. Microbiol. 14: 51–60.
13. Van Damme E. J. M., Peumans W. J., Pusztai A., and Bardocz, S. 1998. Plant lectins: a special class of plant protein, p 1–28. In E. J. M Van Damme., W. J. Peumans, A. Pusztai, and S. Bardocz (ed.) Handbook of plant lectins: properties and biomedical applications. John Wiley and Sons, Chichester, England.
14. Giannasca P. J., Boden J. A., and Monath T. P. 1997. Targeted delivery of antigen to hamster nasal lymphoid tissue with M-cell directed lectins. Infect Immun 65:4288–4298.
15. Bardocz S., Grant G., Pusztai A., Franklin M. F., and Carvalho A de F. F. U. 1996. The effect of phytohemagglutinin at different dietary concentrations on the growth, body composition and plasma insulin of the rat. Br. J. Nutr. 76: 613–626.
16. Eifler R., Pfuller K., Gockeritz W., and Pfuller U. 1994. Improved procedures for isolation of mistletoe lectins and their subunits: lectin pattern of the European mistletoe, p. 144–151. In J. Basu, M. Kundu, and P. Chakrabarty (ed.), Lectins: Biology, Biochemistry, Clinical Biochemistry, Wiley Eastern Limited, New Delhi, India.
17. Ugozzoli M., O'Hagan D. T., and Ott G. S. 1998. Intransal immunization of mice with herpes simplex virus type 2 recombinant gD2: the effect of adjuvants of mucosal and serum antibody responses. Immunology. 93: 563–571.
18. Roberts, M., Bacon, A., Rappuoli, R., Pizza, M., Cropley, I., Douce, G., Dougan, G., Marinaro, M., McGhee, J., and Chatfield, S., 1995. A mutant pertussis toxin molecule that lacks ADP-ribosyltransferase activity, PT-9K/129G is an effective mucosal adjuvant for intransally delivery proteins. Infect. Immun. 63: 2100–2108.
19. Marinaro, M., Di Tommaso, A., Uzzau, S., Fasano, A., and De Magistris, M. T. 1999. Zonula occludens toxin is a powerful mucosal adjuvant for intransally delivered antigens. Infect. Immun. 67: 1287–1291.
20. Fukuta, S., Magnani, J. L., Twiddy, E. M., Holmes, R. K., and Ginsburg, V. 1988. Comparison of the carbohydrate-binding specificities of cholera toxin and Escherichia coli heat-labile enterotoxins Lth-I, LT-IIa and LT-IIb. Infect Immun 56:1748–1753.

21. Fishman, P. H. 1982. Role of membrane gangliosides in the binding and action of bacterial toxins. J. Membrane. Biol. 69: 85–97.
22. Li, T-K., and Fox, B. S. 1996. Cholera toxin B subunit binding to an antigen-presenting cell directly co-stimulates cytokine production from a T cell clone. Int. Immunol. 8: 1849–1856.
23. Takahashi, I., Marinaro, M., Kiyono, H., Jackson, R. J., Nakagawa, L., Fujihashi, K., Hamada, S., Clements, J. D., Bost, K. L., and McGhee, J. R. 1996. Mechanisms for mucosal immunogenicity and adjuvancy of *Escherichia coli* labile entertoxin. J. Infect Dis. 173: 627–635.
24. Douce, G., Fontana, M., Pizza, M., Rappuoli, R., and Dougan, G. 1997. Intransal immunogenicity and adjuvannnnticity of site-directed mutant derivatives of cholera toxin. Infect. Immun. 65:2821–2828.
25. Bussing, A. 1996. Induction of apoptosis by the mistletoe lectins. A review of the mechanisms of cytoxicity mediated by *Viscum album* L. Apoptosis 1: 25–32.
26. Hajito, T., Hostanska, K., Frei, K., Rordorf, C., and Gabius, H. J. 1990. Increased secretion of tumor necrosis factor-alpha, interleukin-1, and interleukin-6 by human mononuclear cells exposed to beta-galactoside-specific lectin from clinically applied mistletoe extract. Cancer Res. 50: 3322–3326.
27. Hajto T., Hostanska K., and Gabius, H. J. 1989. Modulatory potency of the beta-galactoside-specific lectin from mistletoe extract (Iscador) on the host defense system in vivo in rabbits and patients. Cancer Res. 49: 4803–4808.
28. Sugii, S., and Tsuji, T. 1989. Binding specificities of heat-labile enterotoxin isolated from porcine and human enterotoxigenic *escherichiaz coli* for different gangliosides. Ca. J. Microbiol. 35: 670–673.
29. Lycke, N., and Sevennerholm. A.-M. 1990. Presentation of immunogens at the gut and other mucosal surfaces, p. 207–227. In Woodrow, M. Levine (ed.). The Molecular Approach to New and Improved Vaccines. Marcel Dekker Inc., NY.
30. Haas, H., Falcone, F. H., Schramm, G., Haisch, K., Gibbs, B. F., Klaucke, J., Poppelmann, M., Becker, W-M., Gabius, J., and Schlaak, M., 1999. Dietary lectins can induce in vitro release of IL-4 and IL-13 from human basophils. Eur. J. Immunol 29: 918–927.
31. Di Tommaso A., Saletti G., Pizza M., Rappuoli R., Dougan G., Abrignani S., Douce G., and De Magestris M. T. 1996. Induction of antigen-specific antibodies in vaginal secretions by using a nontoxic mutant of heat-labile enterotoxin as a mucosal adjuvant Infect. Immun. 64: 974–979.
32. Shibuya et al., 1987. J. Biol. Chem. 262, 1596–1601.
33. Gribes et al., 1993. Plant Mol. Biol. 22, 1181–86.
34. Citous et al. 1996 Cell. Mol. Biol. 42, 473–76.
35. O'Hagan. 1998. J. Pharm. Pharmacol. 50, 1–10.
36. Marchetti et al. 1998. Vaccine 16, 33–37.
37. Giuliani et al. 1998. J. Exp. Med. 187, 1123–32.
38. Partidos et al. 1999. Imunol. Lett. 67, 209–16.
39. O'Hagan et al. 1991. Vaccine 17, 2229–36.
40. Glenn, G. M., Rao, M., Matyas, G. R. and Alving, C. R. (1998). Skin immunization made possible by cholera toxin. *Nature* 391, 851.
41. Glenn, G. M., Scharton-Kersten, T., Vassell, R., Matyas, G. R. and Alving, C. R. (1999). Transcutaneous immunization with bacterial ADP-ribosylating exotoxins as antigens and adjuvants. *Infect Immun* 67, 1100–1106.
42. Lavelle et al., Mucosal immunogenicity of plant lectins in mice. *Immunology* 99, 30–37, 2000.
43. Lavelle et al., The identification of plant lectins with mucosal adjuvant activity. *Immunology, in press*.

What is claimed is:

1. A method of producing an immune response in a mammal, comprising the step of:

administering mucosally to a mammal an admixture comprising an immunogen and a plant lectin selected from the group consisting of ML-I, ML-II, ML-III, and UEA-I, whereby the mammal produces an immune response to the immunogen which is greater relative to the immune response to the immunogen produced in the absence of the plant lectin.

2. The method of claim 1 wherein the admixture is administered intranasally.

3. The method of claim 1 wherein the plant lectin is ML-I.

4. The method of claim 1 wherein the mammal is selected from the group consisting of a dog, a cat, a mouse, a rat, a rabbit, a guinea pig, a chimpanzee, a baboon, and a human.

5. The method of claim 1 wherein the immune response is a T cell response.

6. The method of claim 5 wherein the T cell response is a Th2 response.

7. The method of claim 5 wherein the T cell response is proliferation of T cells.

8. The method of claim 1 wherein the immune response is an antibody response.

9. The method of claim 8 wherein the response is an IgG response.

10. The method of claim 9 wherein the IgG antibodies are IgG1 antibodies.

11. The method of claim 9 wherein the antibodies are detectable in serum.

12. The method of claim 9 wherein the antibodies are detectable in mucosal secretion.

13. The method of claim 12 wherein the mucosal secretion is obtained from a gut mucosa.

14. The method of claim 1 wherein the admixture comprises two or more different lectins.

15. The method of claim 1 wherein the admixture comprises two or more different immunogens.

16. The method of claim 1 wherein the immunogen is a protein of an infectious agent.

17. The method of claim 16 wherein the infectious agent is a virus.

18. The method of claim 16 wherein the immunogen is a glycoprotein D2 protein from a Herpes simplex virus type 2.

19. The method of claim 2 wherein the admixture is administered using a nasal spray.

20. The method of claim 2 wherein a drop of a liquid containing the admixture is administered.

21. The method of claim 1 wherein at least two doses of the admixture are administered.

22. The method of claim 1 wherein the admixture comprises the immunogen and the plant lectin in a ratio of at least about 1:1.

23. The method of claim 22 wherein the ratio is at least about 10:1.

24. The method of claim 8 wherein an antibody titer is measured using an ELISA.

25. The method of claim 1 wherein the admixture is administered in conjunction with a bioadhesive polymer.

26. The method of claim 1 wherein the admixture is in an enteric formulation.

27. The method of claim 1 wherein the plant lectin is ML-II.

28. The method of claim 1 wherein the plant lectin is ML-III.

29. The method of claim 1 wherein the plant lectin is UEA-I.

30. The method of claim 4 wherein the mammal is a mouse.

31. The method of claim 4 wherein the mammal is a human.

32. The method of claim 8 wherein the antibody response is an IgA response.

33. The method of claim 9 wherein the IgG antibodies are IgG2a antibodies.

34. The method of claim 9 wherein the IgG antibodies are IgG2b antibodies.

35. The method of claim 12 wherein the mucosal secretion is obtained from a vaginal mucosa.

36. The method of claim 12 wherein the mucosal secretion is obtained from an oral mucosa.

37. The method of claim 12 wherein the mucosal secretion is obtained from a nasal mucosa.

\* \* \* \* \*